US00RE36784E

United States Patent [19]

Cho et al.

[11] E Patent Number: Re. 36,784

[45] Reissued Date of Patent: Jul. 18, 2000

[54] CHEMOPROTECTIVE ISOTHIOCYANATES

[75] Inventors: Cheon-Gyu Cho, Seoul, Rep. of Korea; Gary H. Posner, Baltimore, Md.; Paul Talalay, Baltimore, Md.; Yuesheng Zhang, Baltimore, Md.

[73] Assignee: The Johns Hopkins University, Baltimore, Md.

[21] Appl. No.: 08/850,387

[22] Filed: May 2, 1997

Related U.S. Patent Documents

Reissue of:

[64] Patent No.: 5,411,986
Issued: May 2, 1995
Appl. No.: 07/030,610
Filed: Mar. 12, 1993

[51] Int. Cl.[7] ..... A61K 38/43; C07C 331/04

[52] U.S. Cl. ..... 424/94.1; 426/49; 426/52; 426/547; 426/615; 424/648; 424/655; 514/514; 514/515; 558/17

[58] Field of Search ..... 514/514, 515; 558/17; 426/648, 547; 424/94.1, 615, 655, 49, 52

[56] References Cited

U.S. PATENT DOCUMENTS

| | | | |
|---|---|---|---|
| 5,725,895 | 3/1998 | Fahey et al. | 426/49 |
| 5,968,505 | 10/1999 | Fahey et al. | 424/94.1 |
| 5,968,567 | 10/1999 | Fahey et al. | 426/49 |

OTHER PUBLICATIONS

Wattenberg, et al., Inhibitory Effects of Benzyl Isothiocyanate Administered Shortly Before Diethlnitrosamine or Benzo[α]pyrene on Pulmonary and Forestomach Neoplasia in A/J Mice, *Carcinogenesis*, 8(12): 1971–1973, 1987.

Morse, et al,. "Effects of Alkyl Chain Length on the Inhibition of NNK–Induced Lung Neoplasia in A/J Mice by Arylalkyl Isothiocyanates,"*Carcinogenesis*, 10(9):1757–1759, 1989.

Stoner, et al., "Inhibitory Effects of Phenethyl Isothiocyanate on N–Nitrosobenzylmethylamine Carcinogenesis in the Rat Esophagus," *Cancer Research* 51:2023–2068, 1991.

Doerr–O'Rourke, et al., "Effects of Phenethyl Isothiocyanate on the Metabolism of the Tobacco–Specific Nitrosamine 4–(methylnitrosamino)–1(3–pyridyl)–1–butanone by Cultured Rat Lung Tissue," *Carcinogenesis*, 12(6):1029–1034, 1991.

Wattenberg, et al., "Inhibition of Carcinogenic Effects of Polycyclic Hydrocarbons by Benzyl Isothiocyanate and Related Compounds," *J. Natl. Cancer*, 48(2):395–398, 1977.

Sparnins, et al., "Enhancement of Gluthathione S–Transferase Activity of the Mouse Forestomach by Inhibitors of Benzo[α]pyrene–Induced Neoplasia of the Forestomach", *Jncl.*, 66(4):769–771, 1981.

Kjær, et al., "isoThiocyanates XXX. Glucohirsutin, a New Naturally Occurring Glucoside Furnishing (–)–8–Methylsulphiny–octyl isoThiocyanate on Enzymic Hydrolysis", *Acta Chem. Scand.* 12(5):833–838, (1958).

McKay, et al., Bacteriostats. II. The Chemical and Bacteriostatic Properties of Isothiocyanates and their Derivatives, *J. Amer. Chem. Soc.*, 81 (16):4328–4335 (1959).

Kjær, Naturally Derived isoThiocyanates (Mustard Oils) and Their Parent Glucosides, *Progress in the Chemistry of Organic Natural Products*, 18:138–176 (1960).

Mislow, et al., "Diastereoisomerism in 9–Dimethylamino–9, 10–dihydro–4,5–dimethylphenanthrene",*J. Amer. Chem. Soc.*, 87(3):665–666 (1965).

Balenović, et al., "Synthesis of (±) Sulphoraphene", *Tetrahedron*, 22:2139–2143 (1966).

Hansen, et al., "Intramolecular Cyclizations of Thioureas Derived From Sulphoraphene: a Case of Asymmetrically Induced Additions to Vinylic Sulphoxides", *Acta Chemica Scandinavica B*, 28:418–424 (1974).

Lam, et al., "Isolation and Identification of Kahweol Palmitate and Cafestol Palmitate as Active Constituents of Green Coffee Beans That Enhance Gluthathione S–Transferase Activity in the Mouse", *Cancer Research*, 42:1193–1198(1982).

Wattenberg, et al., Inhibiroty Effects of 5–(2–pyraziny)–4–methyl–1,2–dithiol–3–thione(Oltipraz) on Carcinogenesis Induced by Benzo[α]pyrene, Diethylnitrosamine and Uracil Mustare,*Carcinogenesis*, 7(8):1379–1381 (1986).

Prochaska, et al., "Direct Measurement of NAD(P)H:Quinone Reductase from Cells Cultured in Microtiter Wells: A Screening Assay for Anticarcinogenic Enzyme Inducer", *Analytical Biochemistry*, 169:328–336(1988).

Prochaska, et al., "Regulatory Mechanisms of Monofunctional and Bifunctional Anticarcinogenic Enzyme Inducers in Murine Liver", *Cancer Research*, 48:4776–4782 (1988).

Wattenberg, et al., "Chemoprevention of Cancer", *Cancer Research*, 45:1–8 (1985).

Prochaska, "Rapid Detection of Inducers of Enzymes That Protect Against Carcinogens", *Proc. Natl. Acad. Sci. USA*, 89:2394–2398(1992).

The Sproutletter, No. 25, Nov.–Dec. 1984.

"The Sproutletter" May–Jun. 1981, No. 4.

Roy Bruder, Ph.D., Discovering Natural Foods, (including pp. 203–209), Woodbridge Press, 1982.

(List continued on next page.)

*Primary Examiner*—Joseph McKane
*Assistant Examiner*—Ebenezer Sackey
*Attorney, Agent, or Firm*—Foley & Lardner

[57] ABSTRACT

Sulforaphane has been isolated and identified as a major and very potent phase II enzyme inducer in broccoli (Brassica oleracea italica). Sulforaphane is a monofunctional inducer, inducing phase II enzymes selectively without the induction of aryl hydrocarbon receptor-dependent cytochromes P-450 (phase I enzymes). Analogues differing in the oxidation state of sulfur and the number of methylene groups were synthesized, and their inducer potencies were measured. Sulforaphane is the most potent of these analogues. Other analogues having different substituent groups in place of the methylsulfinyl group of sulforaphane were also synthesized and assessed. Of these, the most potent are 6-isothiocyanato-2-hexanone and exo-2-acetyl-6-isothiocyanatonorbornane.

44 Claims, 5 Drawing Sheets

OTHER PUBLICATIONS

Brian R. Clement, Hippocrates Health Program, (including pp. 7–11), Hipprocrates Publications, 1989.
Jethro Kloss, The Back to Eden Cookbook, pp. 61–61, Woodbridge Press, 1974.
Steve Meyerowitz, Sproutmann Kitchen Garden Cookbook, The Sprouthouse, Inc., pp. 178–179, 290, 1994.
Steve Meyerowitz, Sprout It, One week from Seed to Salad, The Sprouthouse, Inc., (including pp. 84–85, 120–123), Jun. 1994.
Steve Meyerowitz, The Complete Guide to Sprouting, Sprouts The Miracle Food, Sproutman Publications, (including pp. 121–2), May 1998.
Esther Munroe, Sprouts to Grow and Eat, (including pp. 2–15). Dec. 1974.
Jean Hewitt, The New York Times New Natural Foods Cookbook:, Avon Books, pp. 200–203, 1982.
Martha H. Oliver, Add a Few Sprouts To Ear Better for Less Money, Pivot Original Health Books, (including pp. 52–53, 118–119), 1975.
James C. Schmidt, Horticulture Facts, "Growing Sprouts Indoors", (Rev. 4/81).
Angnes Toms, The Joy of Eating Natural Foods, The Complete Organic Cookbook, pp. 318–319, Nov. 1971.
Karen Cross Whyte, The Complete Sprouting Cookbook, Troubador Press, (including pp. 57–59), 1973.
Ann Wigmore, The Sprouting Book, Avery Publications, (including pp. 29–37), 1986.
Debra Schwarze, Growing Sprouts, Neb Guide, Jan. 1989.
John Tobe, Sprouts Elixir of Life, 1970.
David Ehrlich with George Wolf, Foreward by Peter Albright, M.D., "The Bowell Book", Schocken Books, 1981.
"The Good News Sprouts Recipe Book" ISGA, Aug. 1992.
Ann Wigmore, "The Hippocrates Diet and Health Program", Avery Publications, 1984.
Sproutletter, #41, Summer, 1989.
The Sproutletter, No. 27, Mar.–Apr. 1985.
Steve Meyerowitz, Growing Vegetables Indoors, 1983.
The Sproutletter, No. 24, Sep.–Oct. 1984.
The Sproutletter, Issue 33, Spring 1987.
The Sproutletter, No. 28, May–Jun. 1985.
The Sproutletter, No. 26, Jan.–Feb. 1985.
The Sproutletter, No. 29, Jul.–Aug. 1985.
Sproutletter, #40, Spring, 1989.
Sproutletter, #44, Mar. 1991.
Sproutletter, #36, Winter, 1988.
Sproutletter, #39, Fall, 1988.
Sproutletter, #43, May/Jun. 1990.
Sproutletterm, #38, Summer, 1988.
Deirdre Purdy, ed., The Summer Kitchen, A Farmers' Market Cookbook, 1981.
Viktoras Kulvinskas, M.S. Co–Director Hippocrates Health Institute, "Love Your Body or how to be a live food lover", 1974.
New Prices—New Products, Jul., 1985.
The Sprout House Newsletter, Issue #15, Aug., 1992.
Complaint for Patent Infringement (Brassica Protection Products, LLC v. The Sproutman, Inc. dated Sep. 20, 1999.
Murry Tizer's Answer, Affirmative Defenses and Counterclaims dated Jun. 28, 1999.
The Sproutman, Inc.'s, Answer, Affirmative Defenses and Counterclaims dated Jun. 28, 1999.
Request for Reexamination of U.S. Patent No. 5,725,895 filed Oct. 11, 1999.

CHEMOPROTECTIVE ISOTHIOCYANATES

Matter enclosed in heavy brackets [ ] appears in the original patent but forms no part of this reissue specification; matter printed in italics indicates the additions made by reissue.

*This application is a Reissue of Ser. No. 08/030,610 filed Mar. 12, 1993, U.S. Pat. No. 5,411,986.*

This invention was made with support from the National Institutes of Health, Grant No. CA44530. The U.S. government therefore retains certain fights in the invention.

TECHNICAL FIELD OF THE INVENTION

This invention relates to compounds which stimulate mammalian enzymes which are involved in detoxication of carcinogens. More specifically, it relates to compounds which induce the activity of quinone reductase[1], glutathione transferases and other phase II enzymes, without inducing the activity of cytochromes P-450.

[1]Abbreviation: QR, quinone reductase [NAD(P)H:(quinone-acceptor)oxidoreductase, EC 1.6.99.2].

BACKGROUND OF THE INVENTION

Extrinsic factors, including personal life-styles, play a major role in the development of most human malignancies (Wynder, et al., J. Natl. Cancer Inst. 58:825–832 (1977); Higginson, et al., J. Natl. Cancer Inst. 63:1291–1298 (1979); Doll, et al., J. Natl. Cancer Inst. 63:1191–1308 (1981)). Cigarette smoking and consumption of alcohol, exposure to synthetic and naturally occurring carcinogens, radiation, drugs, infectious agents, and reproductive and behavioral practices are now widely recognized as important contributors to the etiology of cancer. But perhaps most surprising is the inference that normal human diets play causative roles in more than one-third (and possibly even two-thirds) of human neoplasia (Wynder, et al., J. Natl. Cancer Inst. 58:825–832 (1977); Higginson, et al., J. Natl. Cancer Inst. 63:1291–1298 (1979); Doll, et al., J. Natl. Cancer Inst. 63:1191–1308 (1981)). Our food contains not only numerous mutagens and carcinogens but also a variety of chemicals that block carcinogenesis in animal models (Ames, Science 221:1256–1264 (1983); Ames, et al. Proc. Natl. Acad. Sci. USA 87:7777–7781 (1990); Ames, et al., Proc. Natl. Acad. Sci. USA 87:7782–7786 (1990); Carr, B. I., Cancer 55:218–224 (1985); Fiala, et al., Annu. Rev. Nutr. 5:295–321 (1985); Wattenberg, Cancer Res. Suppl. 43:2448s–2453s (1983); Wattenberg, Cancer Res. 45:1–8 (1985); Wattenberg, et al., Diet, Nutrition and Cancer: 193–203 (1986)). Furthermore, carcinogens can even protect against their own toxic and neoplastic effects or those of other carcinogens—i.e., carcinogens may act as anticarcinogens (Richardson, et al., Cancer Res. 11:274 (1951); Huggins, et al., J. Exp. Med. 119:923–942 (1964); Huggins, et al., J. Exp. Med. 119:943–954 (1964)).

Clearly, dietary modifications modulate cancer risk in various ways: for instance, through changes in caloric intake, by altering the consumption of nutritive and nonnutritive major components, and by providing exposure to numerous minor chemicals that may be genotoxic or protective (Ames, Science 221:1256–1264 (1983); Ames, et al., Proc. Natl. Acad. Sci. USA 87:7777–7781 (1990); Ames, et al., Proc. Natl. Acad. Sci. USA 87:7782–7786 (1990); Carr, Cancer 55:218–224 (1985); Wattenberg, Cancer Res. Suppl. 43:2448s–2453s (1983); Wattenberg, L. W., Cancer Res. 45:1–8 (1985); Wattenberg, et al., Diet, Nutrition and Cancer: 193–203 (1986); Tannenbaum, et al., Adv. Cancer Res. 1:451–501 (1953); National Research Council, Diet, Nutrition and Cancer, (1982); National Research Council, Diet and Health: Implications for Reducing Chronic Disease Risk, (1989); Creasey, Diet and Cancer, (1985); Knudsen, Genetic Toxicology of the Diet, (1986)). Rational recommendations for modifying human diets to reduce the risk of cancer require identification of dietary carcinogens and chemoprotectors, even though interactions among such factors in modulating cancer development are complex (Patterson, et al. Am. J. Public Health 78:282–286 (1988)). Whereas extensive efforts have been made to identify dietary carcinogens and mutagens (Ames, Science 221:1256–1264 (1983); Ames, et al. Proc. Natl. Acad. Sci. USA 87:7777–7781 (1990); Ames, et al., Proc. Natl. Acad. Sci. USA 87:7782–7786 (1990)), chemoprotective components have received far less attention.

Numerous epidemiological studies suggest that high consumption of yellow and green vegetables, especially those of the family Cruciferae (mustards) and the genus Brassica (cauliflower, cress, brussels sprouts, cabbage, broccoli), reduces the risk of developing cancer of various organs (Graham, et al., J. Natl. Cancer Inst. 61:709–714 (1978); Graham, Cancer Res. Suppl. 43:2409s–2413s (1983); Colditz, et al., Am. J. Clin. Nutr. 41:32–36 (1985); Kune, et al., Nutr. Cancer 9:21–42 (1987); La Vecchia, et al., J. Natl. Cancer Inst. 79:663–669 (1987); Le Marchand, et al., J. Natl. Cancer Inst. 81:1158–1164 (1989); You, et al., J. Natl. Cancer Inst. 81:162–164 (1989)). Moreover, administration of vegetables or of some of their chemical components to rodents also protects against chemical carcinogenesis (Wattenberg, Cancer Res. Suppl. 43:2448s–2453s (1983); Wattenberg, Cancer Res. 45:1–8 (1985); Wattenberg, et al., Diet, Nutrition and Cancer 193–203 (1986); Boyd, et al., Food Chem. Toxicol. 20:47–52 (1982)).

Well-documented evidence established that feeding of certain vegetables (e.g., brussels sprouts and cabbage) induces both phase I and phase II enzymes[2] in animal tissues (Conney, et al., Fed. Proc. Fed. Am. Soc. Exp. Biol. 36:1647–1652 (1977); Sparnins, et al., J. Natl. Cancer Inst. 66:769–771 (1981); Sparnins, et al., J. Natl. Cancer Inst. 68:493–496 (1982); Aspry, et al., Food Chem. Toxicol. 21:133–142 (1983); Bradfield, et al., Food Chem. Toxicol. 23:899–904 (1985); Salbe, et al., Food Chem. Toxicol. 24:851–856 (1985); Whitty, et al., Food Chem. Toxicol. 25:581–587 (1987); Ansher, et al., Hepatology 3:932–935 (1983); Ansher, et al., Food Chem. Toxicol. 24:405–415 (1986)) and stimulates the metabolism of drugs in humans (Conney, et al., Fed. Proc. Fed. Am. Soc. Exp. Biol. 36:1647–1652 (1977); Pantuck, et al., Clin. Pharmacol. Ther. 25:88–95 (1979); Pantuck, et al., Clin. Pharmacol. Ther. 35:161–169 (1984)). The elevations of enzymes that metabolize xenobiotics may be highly relevant to the protective effects of vegetables, since relatively modest dietary changes not only affected the metabolism of drugs (Ansher, et al., Food Chem. Toxicol. 24:405–415 (1986)) but also modified the ability of carcinogens to cause tumors in rodents (Tannenbaum, et al., Adv. Cancer Res. 1:451–501 (1953); National Research Council, Diet, Nutrition and Cancer (1982); National Research Council, Diet and Health: Implications for Reducing Chronic Disease Risk (1989); Creasey, Diet and Cancer (1985); Knudsen, Genetic Toxicology of the Diet (1986); Longnecker, et al., Cancer 47:1562–1572 (1981); Fullerton, et al., Proc. Am. Assoc. Cancer Res. 29:147 (1988); Li, et al., Cancer Res. 50:3991–3996 (1990)). There is now very good evidence that when phase II enzymes are induced, animals and cells are protected against the toxic and neoplastic effects of carcinogens. In fact, anticarcinogens have been identified based on their ability to induce phase II enzymes. (Reviewed in Talalay (1992) "Chemical protection against cancer by induction of electrophile detoxication (phase II) enzymes" in Cellular and Molecular Targets of Chemoprevention, (V. E. Steele et al., eds.) CRC Press, Boca Raton, Fla.)

[2]Enzymes of xenobiotic metabolism belong to two families (i) phase I enzymes (cytochromes P-450), which functionalize compounds, usually by oxidation or reduction; although their primary role is to detoxify xenobiotics, several cytochromes P-450 can activate procarcinogens to highly reactive ultimate carcinogens (Miller, et al., Bioactivation of Foreign Compounds, 3–28 (1985)); and (ii) phase II enzymes, which conjugate functionalized products with endogenous ligands (e.g., glutathione, flucuronic acid, sulfate) and serve primarily a detoxification role (Jakoby, et al., J. Biol. Chem. 265:20715–20718 (1990)). Quinone reductase (QR) is considered a phase II enzyme because it has protective functions (Prochaska, et al., Oxidative Stress: Oxidants and Antioxidants, 195–211 (1991)) is induced coordinately with other phase II enzymes, and is regulated by enhancer elements similar to those that control glutathione transferase (Favreau, et al., J. Biol. Chem. 266:4556–4561 (1991)).

There is a need in the art for the identification of specific compounds which are able to exert an anti-carcinogenic effect on mammals. Once identified, these chemoprotective compounds can be used as prophylactic medicaments or as food additives.

SUMMARY OF THE INVENTION

It is an object of the present invention to provide a pharmaceutical composition for cancer prevention.

It is another object of the invention to provide compounds which have cancer chemoprotection activity.

It is yet another object of the invention to provide a method for protecting against cancer development.

It is still another object of the invention to provide a food product which is supplemented with a chemoprotective compound.

These and other objects of the invention are provided by one or more of the embodiments described below. In one embodiment a pharmaceutical composition for cancer prevention is provided. The composition comprises an active ingredient which is sulforaphane ((−)1-isothiocyanato-(4R)-(methylsulfinyl)butane) (CAS 4478-93-7) or an analogue thereof, said analogue having a first moiety which is an isothiocyanate and a second moiety which is a polar functional group, wherein said analogue has a chain of one or more carbon atoms linking said first and said second moieties, and wherein said analogue contains no pyridyl moieties.

In another embodiment of the invention compounds are provided which have cancer chemoprotection activity. The compounds include: 1-isothiocyanato5-methylsulfonylpentane ($CH_3$—$SO_2$—$(CH_2)_5$—NCS) ((GHP 1003), 6-isothiocyanato-2hexanone ($CH_3CO(CH_2)_4NCS$) (GHP 1105), exo-2-acetyl-6-isothiocyanatonorbornane (GHP 1066), exo-2-isothiocyanato-6-methylsulfonylnorbornane (GHP 1068), 6-isothiocyanato-2-hexanol (GHP 1106), 1-isothiocyanato-4-dimethylphosphonyl-butane (GHP 1078), exo-2-(1'-hydroxyethyl)-5-isothiocyanatonorbornane (GHP 1075), exo-2-acetyl-5-isothiocyanatonorbornane (GHP 1067), and cis- or trans-3-(methylsulfonyl)cyclohexylmethylisothiocyanate (GHP 1080 and 1079).

In yet another embodiment of the invention a method for protecting against cancer induction or progression is provided. The method comprises the step of: administering to a mammal a chemoprotective composition consisting essentially of sulforaphane ((−)1-isothiocyanato-(4R)-(methylsulfinyl)butane)or an analogue thereof, said analogue having a first moiety which is an isothiocyanate functionality and a second moiety which is a polar functional group, wherein said analogue has a chain of one or more carbon atoms linking said first and said second moieties, and wherein said analogue contains no pyridyl moieties, in an amount effective in producing a cancer preventive effect.

In still another embodiment of the invention a food product is provided. The product has been supplemented with an active chemoprotective compound, wherein said compound is sulforaphane ((−)1-isothiocyanato-(4R)-(methylsulfinyl)butane) or an analogue thereof, said analogue having a first moiety which is an isothiocyanate functionality and a second moiety which is a polar functional group, wherein said analogue has a chain of one or more carbon atoms linking said first and said second moieties.

These and other objects of the invention provide the public with positive means to lower the risk of developing cancers.

DETAILED DESCRIPTION OF THE INVENTION

Figure 1:
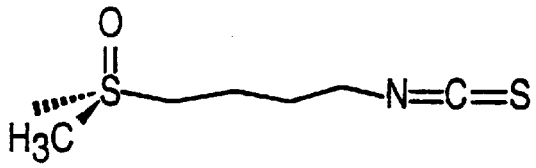
FIG. 1 shows the structure of sulforaphane.

Chemoprotective activities have been detected in certain vegetables which are able to induce the activity of enzymes that detoxify carcinogens (phase II enzymes). One such activity has been detected in broccoli which induces quinone reductase activity and glutathione S-transferase activities in murine hepatoma cells and in the organs of mice. This activity has been purified from broccoli and identified as sulforaphane. Analogues of sulforaphane have been synthesized to determine structure-function relationships.

It is the discovery of the present invention that sulforaphane and its isothiocyanate analogues have chemoprotective activity in excess of previously discovered compounds. The analogues contain a moiety which is a polar functional group. This may be, for example, a sulfoxide, a ketone, a sulfone, a sulfide, a thioester, a thioether, a nitrile, a nitro, a carboxylic ester, a carboxylic acid, a halogen, a phosphine oxide, or a hydroxyl group. The isothiocyanate moiety and the polar functional group are linked by a chain of one or more carbon atoms. Preferably there are at least three carbon atoms in the chain. Typically there are three to five carbon atoms in the chain. The analogues do not contain pyridyl moieties.

The chemoprotective compounds of the present invention can be administered to mammals as a prophylactic against chemically induced cancers. The compounds can be formulated in suitable excipients for oral administration, for topical administration, or for parenteral administration. Such excipients are well known in the art. According to the present invention, pharmaceutical compositions are those which are suitable for administration to humans or other mammals. Typically they are sterile, and contain no toxic, carcinogenic, or mutagenic compounds which would cause an adverse reaction when administered. Administration of the compounds can be performed before, during, or after exposure to the offending carcinogens or procarcinogens. Suitable doses to be administered are those which are sufficient to induce a demonstrable increase of phase II enzymes. This will typically not exceed 500 $\mu$moles per kg per day, but may be much lower.

Sulforaphane and sulforaphene are known to be produced by plants, such as hoary cress, radish and other plants (Mislow, et al. (1965) J. Am. Chem. Soc. 87:665–666; Schmid, et al. (1948) Helvet. Chim. Acta 31:1017–1028; Hansen et al.(1974) Acta Chem. Scand. Ser. B 28:418–424). For the purposes of the present invention, they can be isolated from plants or synthesized. Bertoin, alyssin, erucin, erysolin, iberverin, iberin, and cheirolin can also be isolated from plants; these compounds appear to be less active as inducers than sulforaphane and sulforaphene, at least in cell culture.

Other synthetic analogues of sulforaphane will preferably not be heteroaromatic and more preferably will not be aromatic. Such analogues include olefins, aliphatics, and non-aromatic ring compounds. Some examples of these are shown below in Table 3. The CD value provides a measure of the potency of the compounds as inducers of phase II enzymes, specifically quinone reductase. The preferred compounds of the invention have CD values less than 1, although some established chemoprotectors have higher CD values.

Other analogues of sulforaphane can be used which are not specifically shown. The relative ability of the compound to induce the chemoprotective enzymes can be assessed as taught below, either by testing induction in cell lines, or in whole animals. The compounds can also be tested for the ability to suppress hepatoma formation in rats by 3-methylcholanthrene, 2-acetylaminofluorene, diethylnitrosamine, m-toluenediamine, and azo dyes. They can also be tested for the ability to block the neoplastic effects of diethylnitrosamine or benzo[$\alpha$]pyrene on lung and forestomach of mice or of dimethylbenz[$\alpha$]anthracene (DMBA) on mammary tumor formation in rats.

Also provided by the present invention are food products which have been supplemented with a chemoprotective compound of the present invention. The supplement may be isolated from plants or synthesized.

EXAMPLES

Example 1

This example describes the rapid cell culture assay which was used in the purification of a chemoprotective compound from broccoli.

Assay of Inducer Potency. Inducer activity was measured in Hepa 1c1c7 murine hepatoma cells grown in 96-well microtiter plates (Prochaska and Santamaria, Anal. Biochem. 169:328–336 (1988); Prochaska et al., Proc. Natl. Acad. Sciences USA 89:2394–2398 (1992)). QR activity (based on the formation of the blue-brown reduced tetrazolium dye) was measured with an optical microtiter plate scanner in cell lysates prepared in one plate, and the cell density was determined in the second plate by staining with crystal violet. Quantitative information on specific activity of QR, the inducer potency, and the cytotoxicity of the extract or compound tested is obtained by computer analysis of the absorbances. One unit of inducer activity is defined as the amount that when added to a single microtiter well doubled the QR specific activity. The CD value is the concentration of a compound required to double the quinone reductase specific activity in Hepa 1c1c7 murine hepatoma cells.

Sources of Vegetable and Preparation of Extracts. Vegetables were homogenized with 2 vol of cold water in a Waring Blendor at 4° C. The resultant soups were lyophilized to give dry powders, which were stored at −20° C. Portions (400 mg) of these powders were extracted for 6–24 hr with acetonitrile by shaking in glass vessels at 4° C. The extracts were filtered and evaporated to dryness. The residues were dissolved or suspended in acetonitrile or dimethyl formamide.

The specific activities of QR were raised nearly 6-fold at the highest extract concentrations tested, at which less than 20% cytoxicity was observed. The inductions obtained with broccoli and with other vegetable extracts were proportional to the quantity of extract added over a reasonably wide range. The toxicities of these extracts were modest and were unrelated to their inducer potencies.

Extracts of a series of organically grown vegetables cultivated under a variety of conditions showed large differences in inducer potencies. Although many vegetable extracts induced QR, certain families were consistently more potent inducers. For example, where extracts of several Cruciferae had potent inducer activity, extracts of Solanaceae (peppers, potatoes, tomatoes) had low inducer activity. Of the 24 vegetables examined only 6 showed detectable toxicity; the others were nontoxic at the highest concentrations tested.

Cytotoxicity measurements are important because phase II enzyme inducers may be toxic and/or carcinogenic. Moreover, by use of mutant Hepa cells defective in aryl hydrocarbon receptor or cytochrome P-450 function (Zhang, et al., Proc. Natl. Acad. Sci. USA 89:2399–2403 (1992); Prochaska, et al., Cancer Res. 48:4776–4782 (1988); De Long, et al., Carcinogenesis 8:1549–1553 (1987)), our assay system can distinguish monofunctional inducers (which elevate phase II enzymes selectively), from bifunctional inducers (which elevate both phase I and II enzymes) (Prochaska, et al., Cancer Res. 48:4776–4782 (1988)). Such information is crucial for identification of chemoprotective enzyme inducers for potential use in humans. Ideally, such inducers should be monofunctional, because elevated activities of phase I enzymes may lead to carcinogen activation. The assay of phase II enzymes makes possible further detailed analysis of the effects of treatment of vegetables (e.g., breeding, mutagenesis, growth, storage, and cooking conditions) that might enhance or depress such induction.

Example 2

This example describes the isolation of a potent major phase II enzyme inducer from broccoli.

Fractionation of acetonitrile extracts of SAGA broccoli by preparative reverse-phase HPLC with a water/methanol solvent gradient resulted in recovery of 70–90% of the applied inducer activity in the chromatographic fractions. Surprisingly, the majority (about 65–80% in several chromatographies) of the recovered activity was associated with a single and relatively sharp peak [fractions 18–23; eluted at 64–71% (vol/vol) methanol]. This HPLC procedure was therefore adopted as the first step of the larger-scale isolation of inducer activity.

Lyophilized SAGA broccoli was extracted three times with acetonitrile (35 ml/g) for 6 hr each at 4° C. The pooled extracts were filtered successively through 0.45- and 0.22-μm porosity filters (discarding the insoluble material) and evaporated to dryness under reduced pressure on a rotating evaporator (<40° C.). About 1 g of residue from 640 g of fresh broccoli (64 g of lyophilized powder) contained $3.6\times10^6$ units of inducer activity. The residue was mixed thoroughly with 120 ml of methanol/water (25/75, vol/vol) and the insoluble fraction was discarded. Although not all of the residue obtained from the extraction was soluble in aqueous methanol, the solvent partition procedure resulted in substantial purification without significant loss of inducer activity. Portions of the extract were dried in a vacuum centrifuge and dissolved in small volumes of dimethyl formamide (0.75–1.0 ml per 50 mg of residue), and 50-mg portions were subjected to HPLC (nine runs). Fractions 18–23 from all runs were pooled, evaporated to dryness, applied in acetonitrile to five preparative silica TLC plates (100×200×0.25 mm), and developed with acetonitrile, which was run to the top of each plate three times. Four major fluorescence-quenching components were resolved, and nearly all (99% ) of the inducer activity migrated at $R_f$ 0.4. The active bands were eluted with acetonitrile, pooled, and fractionated by two runs on a second preparative reverse-phase HPLC in a water/acetonitrile gradient (20%–71%). Ultraviolet absorption and inducer activity were eluted in a sharp coincident peak (at 66% acetonitrile) that contained all of the activity applied to the column. Evaporation (<40° C.) of the active fractions gave 8.9 mg of a slightly yellow liquid, which contained 558,000 inducer units (overall yield 15%) and migrated as a single band on TLC.

Example 3

This example describes the identification of the inducer isolated from broccoli, as described in Example 2.

The identify of the inducer was established by spectroscopic methods and confirmed by chemical synthesis. It is (–)-1-isothiocyanato-(4R)-(methylsulfinyl) butane, known as sulforaphane or sulphoraphane (CAS 4478-93-7). See FIG. 1.

Sulforaphane has been synthesized (Schmid, et al., Helv. Chim. Acta 31:1497–1505 (1948) ) and isolated from leaves of hoary cress (Prochazka, Collect. Czech. Chem. Commun. 24:2429–2430 (1959)) and from other plants (Kjaer, et al., Acta Chem. Scand. 12:833–838 (1958)), and the absolute configuration has been assigned (Mislow, et al., J. Am. Chem. Soc. 87:665–666 (1965)). The closely related olefin sulforaphene [4-isothiocyanato-(1R)-(methyl-sulfinyl)-1-(E)butene (CAS 2404-46-8)] has been isolated from radish seeds and other plants (Schmid, et al., Helv. Chim. Acta 31:1017–1028 (1948); Hansen, et al., Acta Chem. Scand. Ser. B 28:418–424 (1974)) and has also been synthesized (Cheung, et al., J. Chem. Soc. Chem. Commun., 100–102 (1965); Balenovic, et al., Tetrahedron 22:2139–2143 (1966)).

Figure 2:
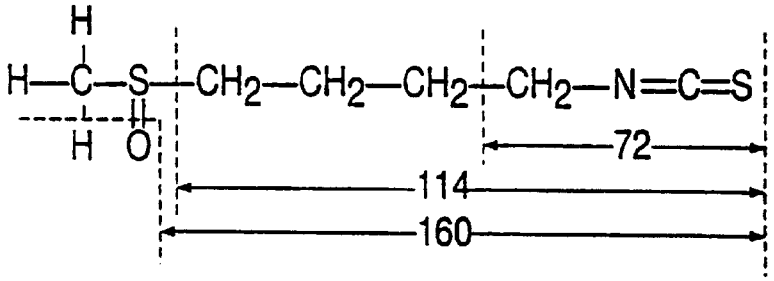
FIG. 2 shows the fragmentation pattern of sulforaphane.
Figure 3:
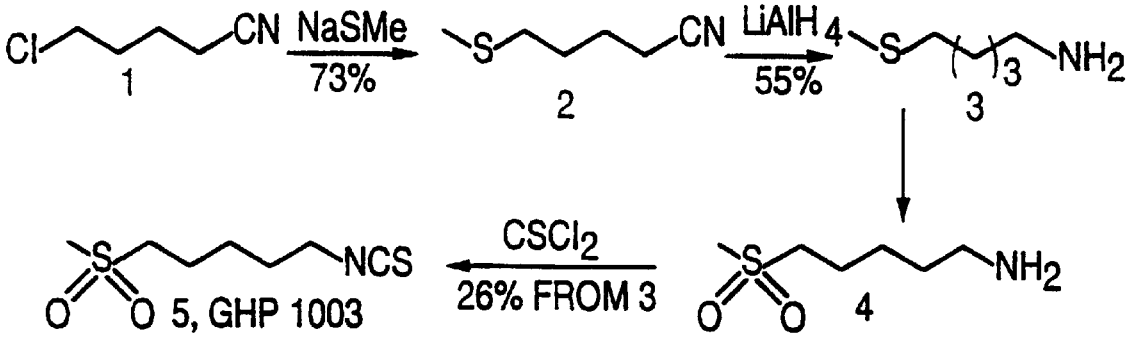
FIG. 3 shows the synthesis of (GHP 1003).
Figure 4:
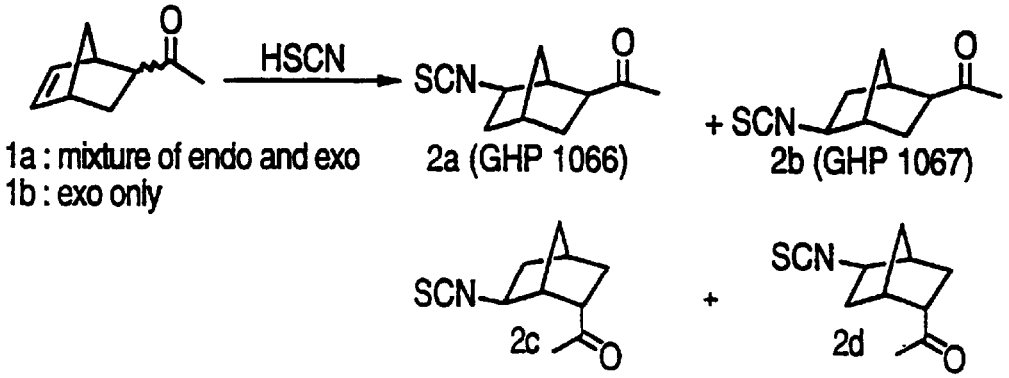
FIG. 4 shows the synthesis of (GHP 1066 and 1067).
Figure 5:
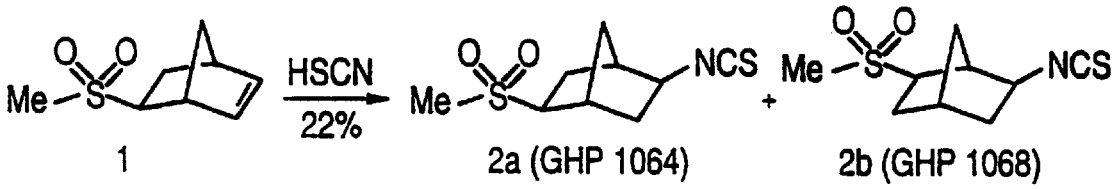
FIG. 5 shows the synthesis of (GHP 1068).
Figure 6:
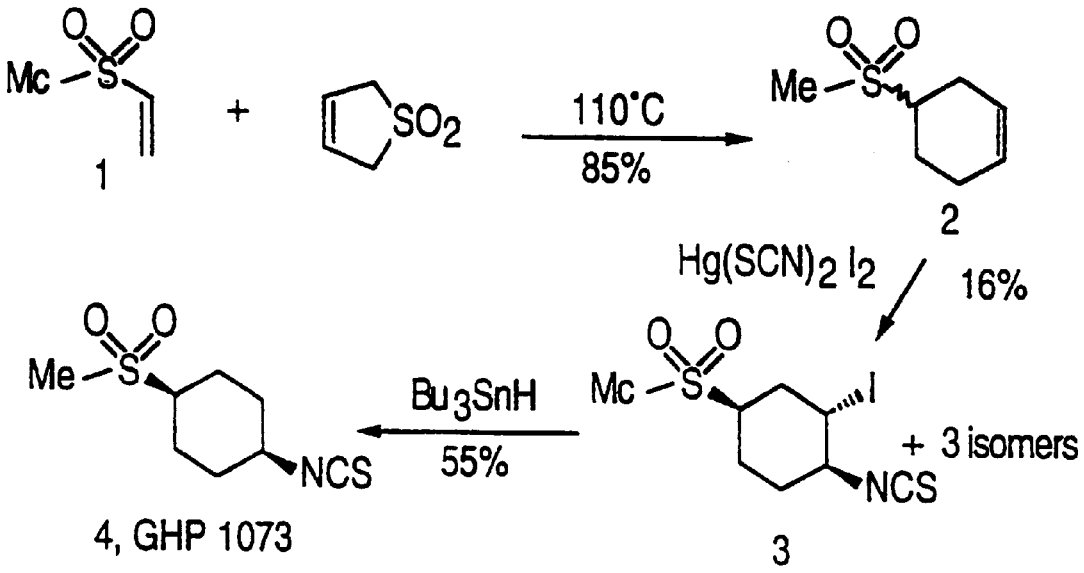
FIG. 6 shows the synthesis of (GHP 1073).
Figure 7:
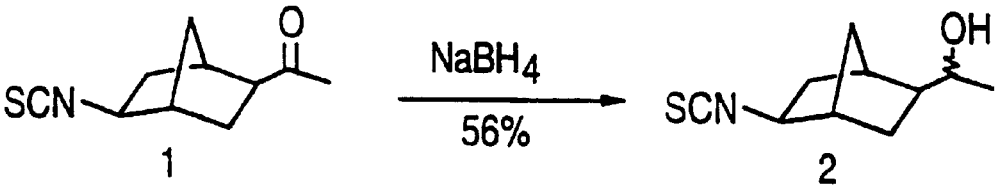
FIG. 7 shows the synthesis of (GHP 1075).
Figure 8:
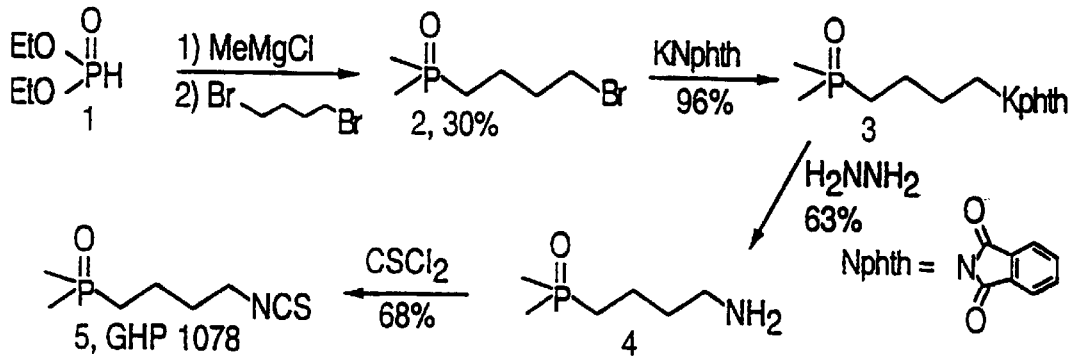
FIG. 8 shows the synthesis of (GHP 1078).
Figure 9:
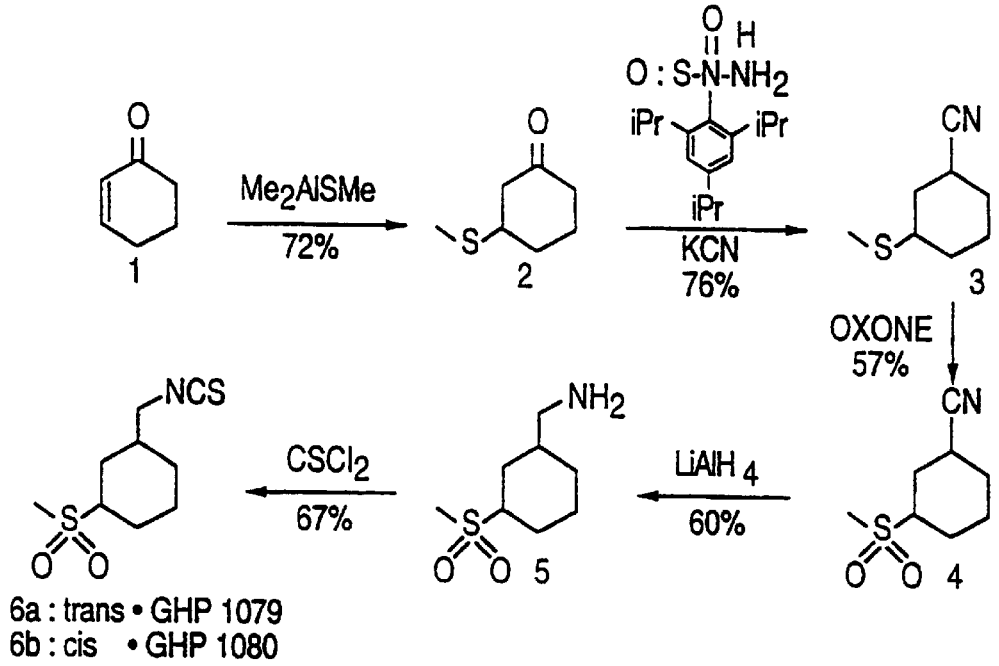
FIG. 9 shows the synthesis of (GHP 1079 and 1080).
Figure 10:
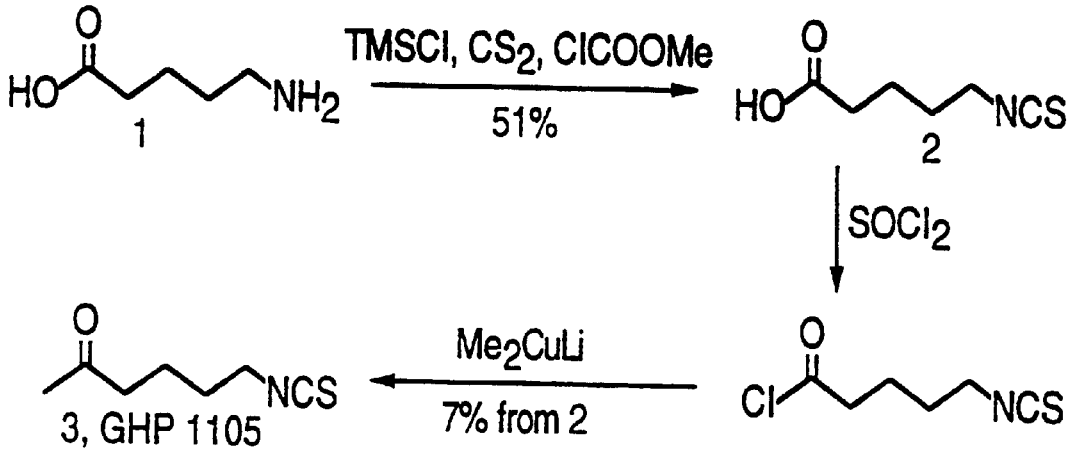
FIG. 10 shows the synthesis of (GHP 1105).
Figure 11:
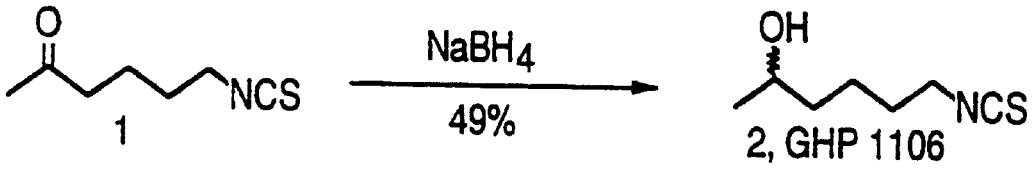
FIG. 11 shows the synthesis of (GHP 1106).

The following evidence establishes that (R)-sulforaphane is the inducer isolated from broccoli, UV spectrum ($H_2O$): $\lambda_{max}$ 238 nm, $\epsilon_{238}$ 910 $M^{-1}cm^{-1}$; addition of NaOH (0.1 M) blue-shifted ($\lambda_{max}$ $_e$226 nm) and intensified ($\epsilon_{226}$ 15,300 $M^{-1}cm^{-1}$) this absorption band, consistent with the behavior of isothiocyanates (Svatek, et al., Acta. Chem. Scan& 13:442–455 (1959)). IR (Fourier transform, neat): strong absorptions at 2179 and 2108 $cm^{-1}$ and also at 1350 $cm^{-1}$, characteristic of isothiocyanates (Kjaer, et al., Acta Chem. Scand. 9:1311–1316 (1955)). $^1H$ NMR (400 MHz, $C^2HCl_3$): δ 3.60 (t, 2H, J=6.1 Hz,—$CH_2$—NCS), 2.80–2.66 (m, 2H, —$CH_2$—SO—, 2.60 (s, 3H, $CH_3$—SO—), and 1.99–1.86 ppm (m, 4H, —$CH_2CH_2$—). $^{13}C$ NMR (400 MHz, $C^2HCl_3$): δ 53.5, 44.6, 38.7, 29.0, and 20.1 ppm. Mass spectrometry (fast atom bombardment; thioglycerol matrix) gave prominent peaks at 178 $(M+H)^+$ and 355 $(M_2+H)^+$. Electron impact mass spectrometry gave a small molecular ion ($M^+$) at 177, and chemical ionization mass spectrometry gave a small molecular ion $(M+H)^+$ at 178 and prominent fragment ions with masses of 160, 114, and 72, consistent with the fragmentation pattern shown in FIG. 2. Precise masses of molecular and fragment ions obtained by electron impact mass spectrometry were 177.0286 (calculated for $C_6H_{11}NOS_2$, 177.0283), 160.0257 (calculated for $C_6H_{10}NS_2$, 160.0255), and 71.9909 (calculated for $C_2H_2NS_1$, 71.9908). In addition, for the mass 160 fragment, the peaks at 161 (M+1) and 162 (M+2) were 8.43% (calculated, 8.44%) and 9.45% (calculated, 10.2%), respectively, of the parent ion. Similarly, for the mass 72 fragment, the peaks at 73 (M+1) and 74 (M+2) were 3.42% (calculated, 3.32% ) and 5.23% (calculated, 4.44% ), respectively, of the parent ion. Hence the isotope compositions corrected for the natural isotope abundance (of $^{13}C$, $^{15}N$, $^{33}S$, and $^{34}S$) were consistent with the relative intensities of the M+1 and M+2 ions of both fragments. The optical rotation of the isolated material was $[\alpha]^{23}_D$–63.6° (c - 0.5, $CH_2Cl_2$), thus establishing that the product is largely, if not exclusively, the (–)-(R) enantiomer $[\alpha]_D$–79°, –73.2°, –66°; refs. 26, 30, and 38, respectively). The spectroscopic properties of synthetic (R,S)-sulforaphane were identical to those of the isolated product.

Example 4

This example describes the synthesis of sulforaphane (CAS 4478-93-7) and its closely related analogs, ibervin, erucin, berteroin, iberin, alyssin, cheirolin, erysolin, and 1-isothiocyanato-5-methylsulfonyl-pentane.

(R,S)-Sulforaphane (CAS 4478-93-7) was prepared according to Schmid and Karrer (Schmid, et al., Helv. Chim. Acta 31:1497–1505 (1948)) except that gaseous thiomethanol was replaced by sodium thiomethoxide. The sulfide analogues, $CH_3$—S—$(CH_2)_n$—NCS, where n is 4 [erucin (CAS 4430-36-8)] or 5 [berteroin (CAS 4430-42-6)] were prepared as described (Kjaer, et al., Acta Chem. Scand. 9:1311–1316 (1955)), and the three-carbon analogue [iberverin (CAS 505-79-3)] was prepared from phthalimidopropyl bromide (Schmid, et al., Helv. Chim. Acta 31:1497–1505 (1948)). IR spectra of all three sulfide analogues showed strong absorptions near 2150 $cm^{-1}$, characteristic of isothiocyanates. $^1H$ NMR spectra of these compounds show sharp singlets at δ 2.10 ppm ($CH_3$—S group). The sulfoxide analogues where n is 3 [iberin (CAS 505-44-2)] or 5 [alyssin (CAS 646-23-1)] were prepared by the same method as sulforaphane. IR spectra of these compounds showed strong absorptions near 2100 $cm^{-1}$, assigned to the —NCS group. $^1H$ NMR spectra also showed sharp singlets around δ 2.5 ppm, consistent with the presence of the $CH_3$—SO group. The sulfone analogues, $CH_3$—$SO_2$—$(CH_2)_n$—NCS, where n is 3 [cheirolin (CAS 505-34-0)], 4[erysolin (CAS 504-84-7), or 5 (unreported) were prepared by known methods (Schneider, et al., Liebigs Ann. Chem. 392:1–15 (1912)). $^1H$ NMR (δ≈2.9 ppm, for $CH_3$—SO—$_2$—) and IR spectra of these compounds were consistent with the structures. Every analogue within this example except 1-isothiocyanato-5-methylsulfonyl-pentane [$CH_3$—$SO_2$—$(CH_2)_5$—NCS] has been isolated from plants (Kjaer, Fortschr. Chem. Org. Naturst. 18:122–176 (1960)).

Example 5

This example describes the inducer activity of the closely-related analogs of sulforaphane whose synthesis is described in the preceding Example.

Each of the analogs of sulforaphane was tested for the ability to induce QR in murine hepatoma cells by the assay described in Example 1. The following structure-function relationships were observed.

The chirality of the sulfoxide does not affect inducer potency, since isolated (R)-sulforaphane and synthetic (R,S)-sulforaphane gave closely similar CD values of 0.2–0.4 $\mu$M. Sulforaphane is therefore the most potent monofunctional inducer that has been identified (Talalay (1989) Adv. Enzyme Regul. 28:237–250; Talalay et al., (1988) Proc. Natl. Acad. Sci. USA 85:8261–82652.[3] Both (R)- and (R,S)-sulforaphane were relatively noncytotoxic: the concentrations required to depress cell growth to one-half were 18 M.

[3]Benzylisothiocyanate has a reported CD value of 1.8 M; phenethylisothiocyanate has a CD of 2.0 M; ethylisothiocyanate has a CD of 30 M; propylisothiocyanate has a CD of 14 M; cyclohexylisothiocyanate has a CD of 14 M.

Sulforaphane and the corresponding sulfone (erysolin) were equipotent as inducers of QR, whereas the corresponding sulfide (erucin) was about one-third as active (Table 1). Oxidation of the side-chain sulfide to sulfoxide or sulfone enhanced inducer potency, and compounds with 4 or 5 methylene groups in the bridge linking $CH_3S$— and —N═C═S were more potent than those with 3 methylene groups.

TABLE 1

Potency of induction of QR in Hepa 1c1c7 cells by sulforaphane and analogues

| Compound | CD value · $\mu$M n = 3 | n = 4 | n = 5 |
|---|---|---|---|
| $CH_3$—S—$(CH_2)_n$—N═C═S | 3.5 (1 berverin) | 2.3 (Erucin) | 1.7 (Berteroin) |
| $CH_3$—S(═O)—$(CH_2)_n$—N═C═S | 2.4 (1 berin) | 0.4–0.8 (Sulforaphane) | 0.95 (Alyssin) |
| $CH_3$—S(═O)(═O)—$(CH_2)_n$—N═C═S | 1.3 (Cheirolin) | 0.82 (Erysolin) | 0.98 |

Mutants of Hepa 1c1c7 cells defective in the Ah (aryl hydrocarbon) receptor or expression of cytochrome P-450IA1 can distinguish monofunctional inducers (which induce phase II enzymes selectively) from bifunctional inducers (which elevate both phase I and II enzymes) (De Long, et al., Carcinogenesis 8:1549–1553 (1987); Prochaska, et al., Cancer Res 48:4776–4782 (1988)). When sulforaphane was tested with the $BP^r$cl mutant (Miller, et al., J. Biol. Chem. 258:3523–3527 (1983)) (defective in transport of the liganded Ah receptor to the nucleus), and the cl mutant (Hankinson et al., (1985) J. Biol. Chem. 260:1790–1795) (which synthesizes inactive cytochrome P-450IA1), induction of QR was normal (dam not shown). Sulforaphane is, therefore, like benzyl isothiocyanate, a monofunctional inducer (Prochaska, et al., Cancer Res 48:4776–4782 (1988)) and is unlikely to elevate activities of cytochromes P-450 that could activate carcinogens.

Example 6

This example demonstrates that the anti-cancer agents of the present invention are active in whole animals as inducers of phase II xenobiotic metabolism enzymes.

When synthetic (R,S)-sulforaphane, erysolin, and erucin were administered to female CD-1 mice by gavage (De Long, et al., Cancer Res. 45:546–551 (1985)), induction of QR and glutathione transferase activities was observed in the cytosols of several organs (Table 2). Sulforaphane and erucin (in daily doses of 15 $\mu$mol for 5 days) raised both enzyme activities 1.6- to 3.1-fold in liver, forestomach, glandular stomach, and mucosa of proximal small intestine, and to a lesser degree in lung. The sulfone (erysolin) was more toxic, but even 5-$\mu$mol daily doses for 5 days elevated the specific activities of these enzymes in some tissues examined. We therefore conclude that sulforaphane and its analogues not only induce QR in Hepa 1c1c7 murine hepatoma cells but also induce both QR and glutathione transferase activities in a number of murine organs.

TABLE 2

Induction of QR and glutathione S-transferase (GST) in mouse tissues by sulforaphane and analogues

| Inducer | Dose · $\mu$mol per mouse per day | Enzyme | Ratio of specific activities (treated/control) Liver | Forestomach | Glandular stomach | Proximal small intestine | Lung |
|---|---|---|---|---|---|---|---|
| $CH_3$—S—$(CH_2)_4$—NCS | 15 | QR | 2.19 ± 0.06 | 1.64 ± 0.18* | 1.72 ± 0.11 | 3.10 ± 0.20 | 1.66 ± 0.13 |
| Erucin | | GST | 1.86 ± 0.08 | 2.51 ± 0.11 | 2.07 ± 0.08 | 3.00 ± 0.21 | 1.41 ± 0.11* |
| $CH_3$—S(═O)—$(CH_2)_4$—NCS | 15 | QR | 2.45 ± 0.07 | 1.70 ± 0.18* | 2.35 ± 0.06 | 2.34 ± 0.19 | 1.37 ± 0.14* |
| | | GST | 1.86 ± 0.08 | 1.98 ± 0.08 | 2.97 ± 0.08 | 2.13 ± 0.20 | 1.17 ± 0.09 |

TABLE 2-continued

Induction of QR and glutathione S-transferase (GST) in mouse tissues by sulforaphane and analogues

| Inducer | Dose · μmol per mouse per day | Enzyme | Ratio of specific activities (treated/control) Liver | Forestomach | Glandular stomach | Proximal small intestine | Lung |
|---|---|---|---|---|---|---|---|
| Sulforaphane 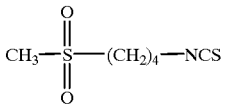 | 5 | QR | 1.62 ± 0.09 | 1.05 ± 0.21 | 1.57 ± 0.08 | 1.22 ± 0.20 | 1.00 ± 0.11 |
| | | GST | 1.08 ± 0.11 | 1.45 ± 0.15 | 1.94 ± 0.10 | 0.87 ± 0.20 | 1.09 ± 0.13 |
| Erysolin | | | | | | | |

The compounds were administered to 6-week-old female CD-1 mice (4 or 5 mice per group) by gavage in indicated single daily doses in 0.1 ml of Emulphor EL 620P (GAF. Linden, NJ) for 5 days. Cytosols were prepared from the tissues 24 hr after the last treatment and assayed for enzyme activities (glutathione S-transferase was measured with 1-chloro-2,4-dinitrobenzene). The specific activities (nmol · $min^{-1}$ · $mg^{-1}$ ± SEM) of organs of vehicle-treatedcontrol mice were as follows. Liver: QR, 47 ± 0.70: GST, 1014 ± 69. Forestomach: QR, 1038 ± 155: GST, 1182 ± 74. Glandular stomach: QR, 3274 ± 85: GST, 1092 ± 81. Small intestine: QR, 664 ±0 119: GST, 1372 ± 266. Lung: QR, 54 ± 5.8: GST. 439 ± 34. Data are presented as mean ± SEM. All ratios were significantly different from 1.0 with $P < 0.01$, except for *$P < 0.05$, and $P > 0.05$.

Example 7

This example describes the synthesis of exo-2-acetyl-6-isothiocyanatonorbornane (GHP 1066 and 1067).

From 1a (mixture)

To a 100 ml 3-neck round bottomed flask equipped with a magnetic stirring bar, dropping funnel and reflex condenser were placed 2.0 g (14.7 mmol) of 2-acetyl-5-norbornene (Aldrich Chemical Co.) and 10 ml of benzene. To this solution was added at room temperature (RT) a mixture of 2.1 g of conc. sulfuric acid and 1.0 ml of water slowly using a dropping funnel. After 4 days at RT, the reaction mixture was filtered through a sintered glass funnel. The filtered white solid was washed with 50 ml of ether. The combined organic solution was then washed with water and brine successively, dried over $MgSO_4$, and concentrated in vacuo to afford a tan oil. Subsequent purification via flash silica-gel column chromatography (20/80, ether/hexane) afforded 1.73 g of product (60% yield, colorless oil) as a mixture of 4 stereoisomers based on $^1H$ NMR analysis (2a: 2b: 2c: 2d 36:39; 8:17). Purification by HPLC (silica-semi prep, 97/3 hexane/EtOAc, 10 ml/min) gave 2a (GHP 1066) in 22% overall yield.

From 1b (exo-only)

The same mixture as the above (1b:0.665 g) was stirred for 40 hr at 50° C. After the same work-up and column chromatography, 0.970 g of product (70% yield) was obtained as a mixture of 4 stereoisomers (2a: 2b: 2c: 2d 32:47; 1:20).

Characterization of 2a (GHP 1066)

$^1H$ NMR (400 MHz, $CDCl_3$) δ 3.64 (dd, J=7.6, J=2.8 Hz, 1H), 2.71(bs, 1H), 2.43(dd, J=4.5 Hz, J=3.6 Hz, 1H), 2.31 (rid, J=8.4 Hz, J=6.0 Hz, 1H), 2.17(s, 3H), 1.83–1.67(m, 2H), 1.58–1.54 (m, 2H), 1.38–1.30(m, 2H); $^{13}C$ NMR ($CDCl_3$) δ 58.4, 50.9, 46.6, 40.0, 35.4, 33.6, 31.5, 28.8 (CO and NCS were not detected); FT-IR ($CHCl_3$, $cm^{-1}$) 2955, 2132, 2085, 1708, 1343; HRMS cald. for $C_{10}H_{13}NOS$ 195.0719, found 195.0719.

Characterization of 2b (GHP 1067)

$^1H$ NMR (400 Mhz, $CDCl_3$) δ3.61 (dd, J=7.2, J=2.8 Hz, 1H), 2.58 (d, J=4.4 Hz, 1H), 2.53 (d, J=4.5 Hz, 1H), 2.35 (dd, J=8.5 Hz, J=3.4 Hz, 1H), 2.16 (s, 3H), 2.0 (dt, J=13.1 Hz, 5.0, 1H), 1.91–1.86 (m, 1H), 1.79–1.75 (m, 1H), 1.55–1.52 (m, 1H), 1.37–1.33 (m, 1H), 1.26–1.22 (m, 1H); FT-IR ($CHCl_3$) 2978 $cm^{-1}$, 2179, 2146, 2085, 1708, 1449, 1343;

Anal. cald. for $C_{10}H_{13}NOS$: C, 61.50; H, 6.71; N, 7.17; S, 16.42 found C, 61.64; H, 6.72; N, 7.12; S, 16.53.

Example 8

This example describes the synthesis of 1-isothiocyanato-5-methylsulfonylpentane (GHP 1003).

Preparation of 2

2 was prepared according to the literature procedure, and the spectral data match the literature values. Kjaer et al. R. Acta. Chem. Scan. 1955, 1311.

Preparation of 3

3 was prepared according to the literature procedure, and the spectral data match the literature values. Kjaer et al., supra.

Preparation of 4

2 was prepared according to the literature procedure, and the spectral data match the literature values.

Preparation of 5 (GHP 1003)

To a flask charged with 50 mg (0.3 mmol) of 4 and 0.8 ml of $H_2O$ were added a solution of 0.03 ml of $CSCl_2$ in 0.3 ml of $CHCl_3$ and 0.5 ml of 5% NaOH at RT. After 30 min, the reaction mixture was extracted with 20 ml of $CH_2Cl_2$ (10 ml×2). The combined organic solution was dried over $MgSO_4$, concentrated in vacuo, and purified by preparative TLC (6/4 EtOAc/hexane) to afford 16 mg (0.08 mmol) of 5 (GHP 1003, 26% from 3) as white solids. $^1H$ NMR (400 MHz, $CDCl_3$) δ 3.50 (t, J=6.4 Hz, 2H), 2.98 (t, J=4.1 Hz, 2H), 2.86 (s, 3H), 1.87–1.82 (m 2H), 1.74–1.66 (m, 2H), 1.58–1.52 (m, 2H); FT-IR 3025 $cm^{-1}$, 2931, 2191, 2097, 1449, 1314, 1132.

Example 9

This example describes the synthesis of exo-2-isothiocyanato-6-methylsulfonylnorbornane (GHP 1068).

Preparation of 2a and 2b

The same procedure as described for GHP 1063 was used except that the reaction mixture was stirred for 6 days at 65° C. After work-up, 2a (17% yield) were isolated by flash column chromatography (silica gel, 100% ether→100% EtOAc). 2a (GHP 1064) was recrystallized from $CH_2Cl_2$/ether/hexane to afford ivy-leaf shaped crystals (mp; 142°–143° C.) in 12% yield. 2b (GHP 1068) was recrystallized from ether to afford small needles (mp; 82°–82.5° C.) in 4% yield.

Characterization of 2a $^1$H NMR (400 MHz, $CDCl_3$) δ 3.66 (t, J=6.8 Hz, 1H), 2.90 (bs 1H), 2.86 (s, 3H), 2.80 (dd, J=8.0 Hz, 2.8, 1H), 2.12 (td, J=14.0 Hz, 5.2, 1H), 2.03 (dt, J=12.0 Hz, 2.2 1H), 1.88–1.62 (m, 5H); FT-IR ($CHCl_3$) 3025 cm$^{-1}$, 2120, 2073, 1320;

Anal. cald. for $C_9H_{13}NO_2S_2$:C, 46.73; H, 5.66; N, 6.06; S;,27.72. found C, 46.74; H, 5.67; N, 6.11; S,27.64.

Characterization of 2b $^1$H NMR (400 MHz, $CDCl_3$) δ 3.65 (dd, J=6.8 Hz, 2.8, 1H), 2.98 (bs, 1H), 2.87 (s, 3H), 2.76 (dd, J=6.8, 1.2, 1H), 2.58 (bs, 1H), 2.06–1.61 (m, 6H); FT-IR ($CHCl_3$) 3025 cm$^{-1}$, 2978, 2191, 2120, 2085, 1349, 1308, 1138.

Example 10

This example describes the synthesis of cis-1-isothiocyanate-4-methylsulfonylcyclohexane (GHP 1073).

Preparation of 2

In an autoclave were placed 11.38 g (94.0 mmol. 10 eq.) of butadiene sulfone, 1.00 g (9.4 mmol) of 1, 0.2 g of hydroquinone as a polymerization inhibitor and 20 ml of absolute EtOH. Upon stirring for 15 min., the reaction mixture was sealed and heated at 110° C. After 60 hr., the reaction mixture was cooled, and poured into 60 ml of 17% $NaHCO_3$. After 10 min., the aqueous solution was extracted with ether (2×50 ml). The combined ether solution was dried over $MgSO_4$, concentrated and chromatographed (60/40 ether/hexane) to afford 1.30 g (8.1 mmol, 85% yield) of 2 as a brown oil. An aliquot was distilled under the reduced pressure to give a colorless liquid for analysis.

Preparation of 3

To a flask charged with 342 mg (0.63 mmol) of Hg $(SCN)_2$ was added a premixed solution of $I_2$ in 8 ml of benzene. After 30 min. at room temperature (RT), to the mixture was added 202 mg (1.26 mmol) of 2 dissolved in 1 ml of benzene, and the flask containing the reaction mixture was wrapped with aluminum foil and stirred for 7.5 days at RT under argon atmosphere. The reaction mixture was then diluted with 20 ml of ether, washed with aqueous KI, $Na_2S_2O_3$, brine, dried over, and concentrated in vacuo. Flash column chromatography (1/1 ether/hexane) afforded 20 mg (0.06 mmol) of 3 (5% yield) as an oil along with 3 other isomers (11% yield).

Preparation of 4

To a flask charged with 21 mg (0.07 mmol) of 3 and 1 ml of benzene was added 0.05 ml (0.2 mmol, 3 eq.) of $Bu_2SnH$ at RT. After 10 hr., the reaction mixture was treated with 35 mg of DBU (1,8-diazabicyclo[5,4,0]undec-7-ene)and 1 ml of wet ether. The resulting mixture was filtered off, concentrated and chromatographed (100% ether→100% EtOAc) to afford 7.3 mg (0.03 mmol) of 4 (GHP 1073, 55% yield) as a white solid (mp; 123° C.).

Characterization of 4

$^1$H NMR (400 MHz, $CDCl_3$) δ 4.09 (t, J=3.2 Hz, 1H), 2.86 (s, 3H), 2.87–2.80 (m, 1H), 2.23–2.20 (m, 4H), 1.96–1.85 (m, 2H), 1.71–1.59 (m, 2H); FT=IR ($CHCl_3$) 3025 cm$^{-1}$, 2943, 2085, 1302.

Example 11

This example describes the synthesis of exo-2-(1'-hydroxyethyl)-5-isothiocyanatonorbornane (GHP 1075).

To a flask charged with 37.3 mg (0.19 mmol) of 1 (GHP 1067) and 1.5 ml of MeOH was added 11.0 mg (0.29 mmol) of $NaBH_4$ at 0° C. After 20 min., the excess $NaBH_4$ was quenched with a few drops of $H_2O$, diluted with either, dried over $MgSO_4$, and concentrated in vacuo. Preparative TLC (80/20 ether/hexane) afforded 21 mg (0.11 mmol) of 2 (GHP 1075, 56% yield) as a white solid (mixture of 2 disastereomers based on $^1$H NMR).

$^1$H NMR (400 Mhz, $CDCl_3$) δ 3.58–3.54 (m), 3.49–3.45 (m), 3.39–3.32 (m), 2.54–2.46 (m), 2.18–2.16(d), 1.80–1.65 (m), 1.55–1.20 (m), 1.19 (d, J=6.0 Hz); FT-IR ($CHCl_3$) 3613 cm$^{-1}$, 2966, 2872, 2097, 1343.

Example 12

This example describes the synthesis of 1-isothiocyanato-4-dimethylphosphonyl-butane (GHP 1078).

Preparation of 2

To a 25 ml flame dried round bottomed flask charged with 15.2 ml (45.6) mmol) of MeMgCl (Aldrich Chemical Co., 3.0 M in THF) was added 1.5 ml (11.41 mmol) of diethyl phosphite 1 while the internal temperature was maintained around 25° C. with occasional cooling with ice-water bath. After 1 hr, the mixture was cannulated into the flask charged with 2.55 ml (22.82 mmol) of dibromobutane and 15 ml of THF at 0° C. under Ar atmosphere. Upon addition, the reaction mixture was heated under reflux for 5 hr, cooled, and dumped into 30 ml of cold dil. HCl. The resulting aqueous solution was extracted with $CHCl_3$ (3×50 ml), and the organic solution was washed with sat. $k_2CO_3$, dried over $K_2CO_3$, and concentrated in vacuo to give 2.48 g of crude product as a tan oil. Purification by flash column chromatography (silica-gel, 8/2 EtOAc/MeOH→6/4 EtOAc/hexane) afforded 0.72 g (3.42 mmol) of 2 as a colorless oil.

Preparation of 3

In a 100 ml round bottomed flask were placed 0.733 g (3.44 mmol) of 2, 0.766 g of potassium phthalimide and 20 ml of DMF. The mixture was heated under reflux for 4 hr, cooled and dumped into 60 ml of $CHCl_3$. The organic solution was washed with $H_2O$ dried over $NaHCO_3$, and concentrated in vacuo to afford 0.92 g of 3 as a white solid (used for next reaction without further purification).

Preparation of 4

To a flask charged with 0.1 g of 3 was added 4 ml of methanolic hydrazine (0.2M) at RT. After 14 hr at RT, the reaction mixture was concentrated, and the residue was treated with 5 ml of 1N Hcl, washed with $CHCl_3$, strongly basified with solid NaOH. The basified solution was then extracted with $CHCl_3$ (2×20 ml), and the combined organic solution was dried over $K_2CO_3$, and concentrated in vacuo to 33 mg (0.22 mmol) of 4 as a white solid (used for next reaction without further purification).

Preparation of 5 (GHP 1078)

To a flask charged with 33 mg (0.22 mmol) of 4 and 1 ml of $CHCl_3$ were added at RT 0.02 ml (0.27 mmol) of $CSCL_2$ and 0.3 ml of 1N NaOH. After 35 min at RT, the reaction mixture was partitioned between 10 ml $CHCl_3$ of and 10 ml $H_2O$. The separated organic layer was dried over $MgSO_4$, concentrated in vacuo and chromatographed (silica-gel, 8/2 EtOAc/MeOH) to afford 29 mg (0.15 mmol) of 5 (GHP 1078) as a reddish yellow oil. $^1$H NMR (400 MHz, $CDCl_3$) δ 3.54 (t, J=6.0 Hz, 2H), 1.82–1.70 (m, 6H), 1.48 (s, 3H), 1.44 (s, 3H); FT-IR ($CHCl_3$) 2941 cm$^{-1}$, 2191, 2097, 1302, 1173; $^{13}$C NMR (400 MHz $CDCl_3$) δ 44.5, 30.6 (d, J=20.2 Hz, 1C), 30.7 (d, J=34.7 Hz, 1C), 19.3, 16.2 (d, J=69 Hz, 2C); $^{31}$P NMR ($CDCl_3$) δ46.1; HRMS cald. for $C_3H_{14}NOPS$ 191.0534, found 195.0536.

Example 13

This example describes the synthesis of cis- or trans-3-(methylsulfonyl)cyclohexylmethylisothiocyanate (GHP 1079 or 1080).

Preparation of 2

2 was prepared according to the literature procedure, and the spectral data matched the literature values. Kozikowski, A.; Ames, A. Tetrahedron 1985, 4821.

Preparation of 3

To a 100 ml round bottomed flask were placed 0.438 g (3.0 mmol) of 2, 1.418 g of 2,4,6-triisopropylbenzenesulfonohydrazide (prepared according to literature procedure; Jirieny, J.; Orere, D.; Reese, C. J. Chem. Soc. Perkin Trans. I, 1980, 1487) and 8 ml of MeOH at RT. After 1 hr, 0.739 g of KCN was added at RT, and the resulting mixture was heated under gentle reflux for 3 hr. The reaction mixture was cooled, diluted with 20 ml of $H_2O$, and extracted with $CH_2Cl_2$ (2×20 ml). The organic solution was subsequently washed with aq. $NaHCO_3$, dried over $MgSO_4$, concentrated in vacuo and purified by flash column chromatorgraph (8/2 hexane/EtOAc) to afford 0.360 g (2.3 mmol) of 3 (76% yield) as a yellow oil.

Preparation of 4

To a flask charged with 0.36 g (2.32 mmol) of 3 and 10 ml of aqueous MeOH (9/1 v/v MeOH/$H_2O$) was added 2.75 g (4.64 mmol) of OXONE (2$KHSO_5$. $KHSO_4K_2SO_4$) at RT. After 24 hr, the reaction mixture was filtered through a sintered glass funnel, and the filtered solid material was washed with 50 ml of $CHCl_3$. The combined organic solution was washed with $H_2O$, dried over $MgSO_4$ and concentrated in vacuo to afford 0.246 g (1.31 mmol) of 4 (57% yield) as a colorless oil. This material was used in the next reaction without purification.

Preparation of 5

To a $LiAlH_4$ suspension in 10 ml of anhydrous ether was cannulated 0.246 g (1.31 mmol) of 4 dissolved in 3 ml of THF at RT. Upon addition, the reaction mixture was heated under reflux. After 2.5 hr, the reaction mixture was cooled, quenched with 0.5 ml of $H_2O$ and 0.5 ml of 5% of NaOH, and filtered through a sintered glass funnel. The solid material filtered was thoroughly washed with ether. The combined organic solution was dried over $K_2CO_3$ and concentrated in vacuo to afford 0.15 g (0.78 mmol) of 5 (60% yield) as a colorless oil. This material was used in the next reaction without purification.

Preparation of 6a (GHP 1079) and 6b (GHP 1080)

To a flask charged with 0.15 g (0.78 mmol) of 5 and 3 ml of $CHCl_3$ were added 0.07 ml of $CSCl_2$ and 1.5 ml of 5% of NaOH at RT. After 1 hr, the reaction mixture was diluted with 10 ml of $CH_2Cl_2$, washed with $H_2O$ and brine, dried over $MgSO_4$. concentrated in vacuo, and chromatographed (silica-gel, 1/1 hexane/EtOAc) to give 0.123 g (0.53 mmol) of products 67% yield) as a mixture 6a and 6b (1:1 ratio). HPLC (40/60 EtOAc/hexane) separation afforded GHP1079 and GHP 1080 (both as colorless oil). 6a (GHP 1079): $^1H$ NMR (400 MHz, $CDCl_3$) δ3.50 (d, J=6.8 Hz, 2H), 3.09–3.03 (m, 1H), 2.88 (s, 3H), 2.45–2.37 (m, 1H), 2.14–2.07 (m, 1H), 1.98–1.84 (m, 4H), 1.74–1.66 (m, 1H), 1.59–1.4 (m, 2H); FT-IR ($CHCl_3$) 3013 $cm^{-1}$, 2943, 2872, 2191, 2097, 1449, 1308; $^{13}C$ NMR ($CDCl_3$) δ2.6, 43.5, 33.6, 28.0, 22.5, 22.1, 19.5, 14.9; HRMS calc. 233.0544 found 233.0545. 6b (GHP 1080): $^1H$ NMR (400 MHz, $CDCl_3$) δ3.47 (d, J=6.0 Hz, 2H), 2.92–2.82 (m, 1H), 2.84 (s, 3H), 2.28–2.20 (m, 2H), 2.04 (tt, J=6.8 Hz, 3.0, 1H), 1.87–1.75 (m, 2H), 1.53–1.27 (m, 3H), 1.06 (tq, J=12.2 Hz, 3.6, 1H); FT-1R ($CHCl_3$) 3025 $cm^{-1}$, 2931, 2861, 2191, 2097, 1449, 1308; $^{13}C$ NMR ($CDCl_3$) δ56.5, 45.5, 32.6, 32.5, 23.9, 23.8, 20.0, 19.1; HRMS calc. 233.0544 found 233.0548.

Example 14

This example describes the synthesis of 6-isothiocyanato-2-hexanone ($CH_3CO(CH_2)_4NCS$)(GHP 1105).

Preparation of 2

To a flask charged with 2.252 g (19.22 mmol) of 1 and 20 ml of chloroform were added 40 ml of TMSCl. The mixture was heated around 45° C., then cooled to room temperature (RT). To this mixture was added 1.21 ml of $CS_2$ at RT, and the resulting solution was cooled to 0° C. and treated with 8 ml of $Et_3N$. After 10 min, the reaction mixture was warmed to RT, and stirred for 2 hr, then cooled to 0° C., and treated with 2.0 ml of methyl chloroformate. After 45 min at 0° C., the reaction mixture was armed at RT, diluted 75 ml of hexane, filtered off, and concentrated in vacuo. The residue was dissolved in 75 ml of THF at 0° C., then 7 ml of $H_2O$ was added to it. After 1.5 days, the reaction was dried over $MgSO_4$, concentrated and chromatographed (silica-gel, 20/80 EtOAc/hexane→1/1 EtOAc/hexane) to afford 1.563 g (9.80 mmol) of 2.

Preparation of 3 (GHP 1105)

A mixture of 0.3 g (1.89 mmol) of 2, 0.18 ml of $SOCl_2$ and 10 ml of $CHCl_3$ was heated under reflux for 2 hr. Upon removal of solvent, the residue was redissolved with 2 ml of dry ether. To this solution was added $Me_2CuLi$ (prepared from CuI and 2MeLi in ether) at −78° C. After 2 hr at −78° C., the reaction mixture was quenched with sat. $NH_4Cl$, warmed to RT, and extracted with ether. The organic solution was dried over $MgSO_4$, concentrated in vacuo, and chromatographed (silica-gel, 30/70 ether/hexane) to afford 0.022 g (0.13 mmol) of 3 (7% yield from 2) as an oil. $^1H$ NMR (300 MHz, $CDCl_3$) δ3.55–3.49 (m, 2H0, 2.53–2.47 (m, 2H0, 2.16 (s, 3H), 1.72–1.68 (m, 4H0; FT-IR ($CHCl_3$) 3019 $cm^{-1}$, 2191, 2112, 1715, 1224.

Example 15

This example describes the synthesis of 6-isothiocyanato-2-hexanol (GHP 1106).

To a flask charged with 15.0 mg (0.1 mmol) of 1 and 2 ml of EtOH was added 3.6 mg (0.1 mmol) of NaBH4 at 0° C. After 10 min, the reaction mixture was treated with 20 drops of $H_2O$, dried over $MgSO_4$, concentrated in vacuo, and chromatographed (30/70 ether/hexane) to afford 7.5 mg (0.05 mmol) of 2 (GHP 1106, 49% yield) as a liquid.

$^1H$ NMR (400 MHz, $CDCl_3$) δ3.87–3.77 (m, 1H), 3.53 (t, J=6.6 Hz, 2H), 1.78–1.68 (m, 2H), 1.50–1.35 (m, 4H), 1.21 (d, 6.2 Hz, 3H); FT-IR ($CHCl_3$) 3615 $cm^{-1}$, 2945, 2180, 2107, 1375.

Example 16

This example describes the relative inducer activity of a large variety of sulforaphane analogs.

Analogs were synthesized and tested in the hepatoma cell assay described in Example 1. The results are shown in Table 3.

TABLE 3
| | STRUCTURE | CD (μM) |
|---|---|---|
| GHP 1001 | 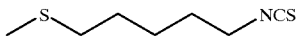 | 1.71 |
| GHP 1002 | 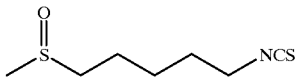 | 0.94 |
| GHP 1003 | 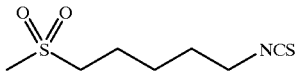 | 0.98 |
| GHP 1004 | 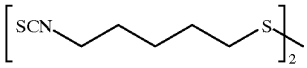 | 0.83 |
| GHP 1005 | 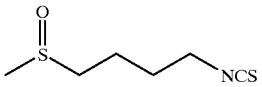 sulforaphane | 0.20 |
| GHP 1006 | 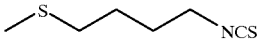 | 2.30 |
| GHP 1007 | 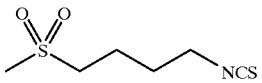 | 0.82 |
| GHP 1008 | 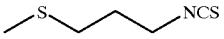 | 3.52 |
| GHP 1009 | 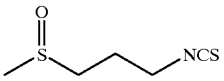 | 2.36 |
| GHP 1010 | 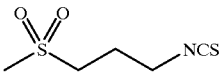 | 1.32 |
| GHP 1021 | 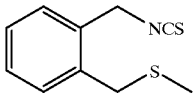 | 4.3 |
| GHP 1022 | 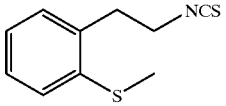 | 7.4 |
| GHP 1023 | 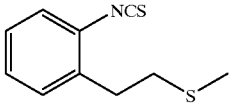 | 100 |
| GHP 1031 | 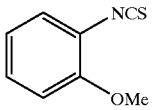 | 100 |
TABLE 3-continued
| | STRUCTURE | CD (μM) |
|---|---|---|
| GHP 1032 | 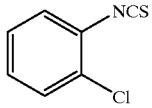 | 100 |
| GHP 1033 | 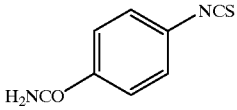 | 100 |
| GHP 1041 | 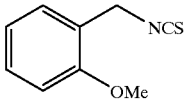 | 2.41 |
| GHP 1042 | 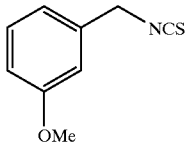 | 8.65 |
| GHP 1043 | 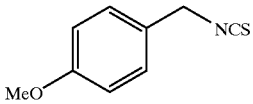 | 25 |
| GHP 1044 | 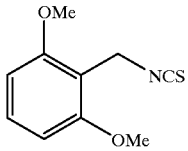 | 5.8 |
| GHP 1045 | 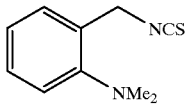 | 12.5 |
| GHP 1046 | 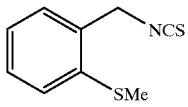 | 6.8 |
| GHP 1047 | 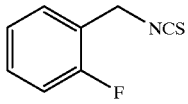 | 13.1 |
| GHP 1048 | 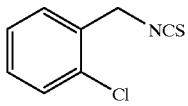 | 14.1 |
| GHP 1049 | 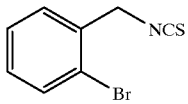 | 12.5 |

TABLE 3-continued
| | STRUCTURE | CD (μM) |
|---|---|---|
| GHP 1050 | 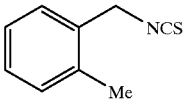 | 3.7 |
| GHP 1051 | 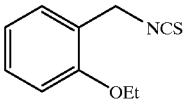 | 2.5 |
| GHP 1052 | 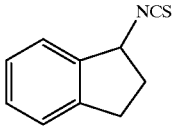 | 38.9 |
| GHP 1053 | 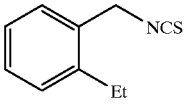 | 12.5 |
| GHP 1061 | 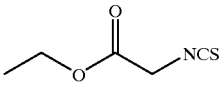 | 8.2 |
| GHP 1062 | 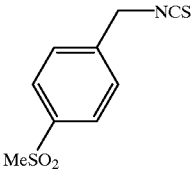 | 1.2 |
| GHP 1063 | 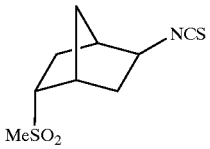 | 1.02 |
| GHP 1064 | 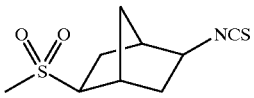 | 0.66 |
| GHP 1065 | 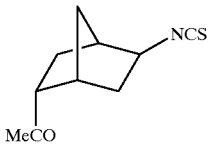 | 0.77 |
| GHP 1066 | 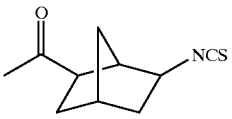 | 0.26 |
| GHP 1067 | 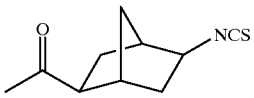 | 0.43 |
TABLE 3-continued
| | STRUCTURE | CD (μM) |
|---|---|---|
| GHP 1068 | 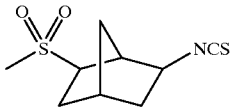 | 0.15 |
| GHP 1069 | 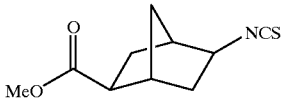 | 0.68 |
| GHP 1070 | 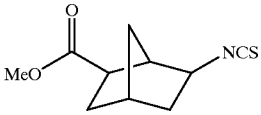 | 1.6 |
| GHP 1071 | 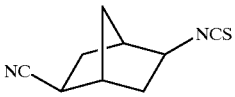 | 0.59 |
| GHP 1072 | 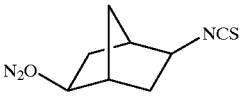 | 1.05 |
| GHP 1073 | 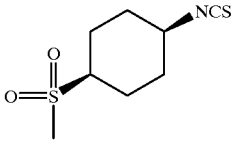 | 0.44 |
| GHP 1074 | 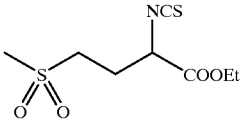 | 2.64 |
| GHP 1075 | 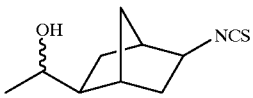 | 0.45 |
| GHP 1076 | 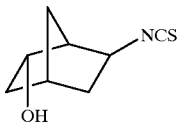 | 1.10 |
| GHP 1077 | 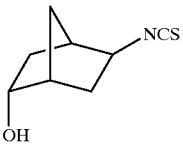 | 1.85 |
| GHP 1078 | 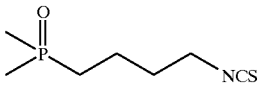 | 0.43 |

TABLE 3-continued

| | STRUCTURE | CD (μM) |
|---|---|---|
| GHP 1079 | 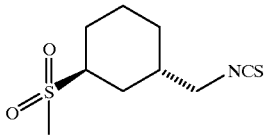 | 0.48 |
| GHP 1080 | 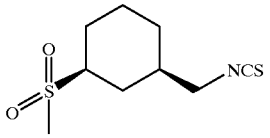 | 0.41 |
| GHP 1081 | 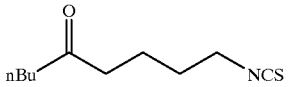 | 2.0 |
| GHP 1101 | 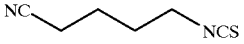 | 1.97 |
| GHP 1102 | 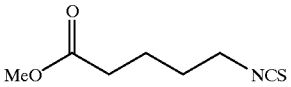 | 2.81 |
| GHP 1103 | 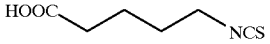 | 2.19 |
| GHP 1104 | 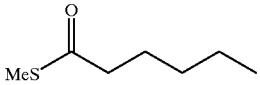 | 2.8 |
| GHP 1105 | 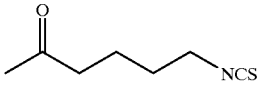 | 0.23 |
| GHP 1106 | 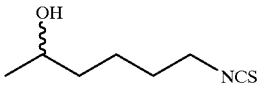 | 0.35 |

We claim:

1. A [pharmaceutical] composition comprising [an active ingredient which is] *an analogue of* sulforaphane ((−)1-isothiocyanato-(4R)-(methylsulfinyl)butane) [(CAS 4478-93-7) or an analogue thereof], said analogue being selected from the group consisting of: 6-isothiocyanato-2-hexanone [(GHP 1105)]; exo-2-acetyl-6-isothiocyanatonorbornane [(GHP 1066)]; exo-2-isothiocyanato-6-methylsulfonylnorbornane [(GHP 1068)]; 6-isothiocyanato-2-hexanol [(GHP 1106]: 1-isothiocyanato-4-dimethylphosphonylbutane [(GHP 1078)]; exo-2-(1'-hydroxyethyl)-5-isothiocyanatonorbornane [(GHP 1075)]; exo-2-acetyl-5-isothiocyanatonorbornane [(GHP 1067)]: 1-isothiocyanato-5-methylsulfonylpentane [(GHP 1003)]; and cis- or trans-3-(methylsulfonyl)cyclohexylmethylisothiocyanate [(GHP 1079 or 1080)].

[2. The pharmaceutical composition of claim 1 wherein said active ingredient is sulforaphane.]

[3. The pharmaceutical composition of claim 1 wherein said active ingredient is selected from the group consisting of: 6-isothiocyanato-2-hexanone (GHP 1105); exo-2-acetyl-6-isothiocyanatonorbornane (GHP 1066); exo-2-isothiocyanato-6-methylsulfonylnorbornane (GHP 1068); 6-isothiocyanato-2-hexanol (GHP 1106); 1-isothiocyanato-4-dimethylphosphonylbutane (GHP 1078); exo-2-(1'-hydroxyethyl)-5-isothiocyanatonorbornane (GHP 1075); exo-2-acetyl-5-isothiocyanatonorbornane (GHP 1067); 1-isothiocyanato-5-methylsulfonylpentane (GHP 1003); and cis- or trans-3-(methylsulfonyl)cyclohexylmethylisothiocyanate (GHP 1079 or 1080).]

[4. The pharmaceutical composition of claim 1 further comprising a pharmaceutically acceptable excipient.]

5. A compound consisting of: 1-isothiocyanato-5-methylsulfonylpentane ($CH_3$—$SO_2$—$(CH_2)_5$—NCS) [((GHP 1003)].

6. A compound consisting of: 6-isothiocyanato-2-hexanone ($CH_3CO(CH_2)_4NCS$) [(GHP 1105)].

7. A compound consisting of: exo-2-acetyl-6-isothiocyanatonorbornane [(GHP 1066)].

8. A compound consisting of: exo-2-isothiocyanato-6-methylsulfonylnorbornane [(GHP 1068)].

9. A compound consisting of: 6-isothiocyanato-2-hexanol [(GHP 1106)].

10. A compound consisting of: 1-isothiocyanato-4-dimethylphosphonylbutane [(GHP 1078)].

11. A compound consisting of: exo-2-(1'-hydroxyethyl)-5-isothiocyanatonorbornane [(GHP 1075)].

12. A compound consisting of: exo-2-acetyl-5-isothiocyanatonorbornane [(GHP 1067)].

13. A compound consisting of: cis-or trans-3-(methylsulfonyl)cyclohexylmethylisothiocyanate [(GHP 1079 or 1080)].

14. A method for suppressing the formation of chemically-induced mammary tumors or hepatomas, comprising:

administering to a mammal a chemoprotective composition [consisting essentially of] *comprising an analogue of* sulforaphane ((−)1-isothiocyanato-(4R)-(methylsulfinyl)butane) [or an analogue thereof], said analogue being selected from the group consisting of: 6-isothiocyanato-2-hexanone [(GHP 1105)]; exo-2-acetyl-6-isothiocyanatonorbornane [(GHP 1066)]; exo-2-isothiocyanato-6-methylsulfonylnorbornane [(GHP 1068)]; 6-isothiocyanato-2-hexanol [(GHP 1106)]: 1-isothiocyanato-4-dimethylphosphonylbutane [(GHP 1078)]; exo-2-(1'-hydroxyethyl)-5-isothiocyanatonorbornane [(GHP 1075)]: exo-2-acetyl-5-isothiocyanatonorbornane [(GHP 1067)]: 1-isothiocyanato-5-methylsulfonylpentane [(GHP 1003)]; and cis- or trans-3-(methylsulfonyl) cyclohexylmethylisothiocyanate [(GHP 1079 or 1080)], in an amount effective in producing a mammary tumor or hepatoma formation suppressing effect.

*15. A composition comprising an active ingredient which is sulforaphane ((−)1-isothiocyanato-(4R)-(methylsulfinyl)(butane) or an analogue thereof, said analogue being selected from the group consisting of: 6-isothiocyanato-2-hexanone; exo-2-acetyl-6-isothiocyanatonorbornane; exo-2-isothiocyanato-6-methylsulfonylnorbornane; 6-isothiocyanato-2-hexanol; 1-isothiocyanato-4-dimethylphosphonylbutane; exo-2-(1'-hydroxyethyl)-5-isothiocyanatonorbornane; exo-2-acetyl-5-isothiocyanatonorbornane; 1-isothiocyanato-5-methylsulfonylpentane; and cis- or trans-3-(methylsulfonyl) cyclohexylmethylisothiocyanate, and a suitable excipient.*

*16. A method of chemoprotection comprising the steps of:*

*(a) synthesizing sulforaphane or an isothiocyanate analogue thereof, or purifying sulforaphane or an isothiocyanate analogue thereof from a natural source; and*

(b) providing said sulforaphane or isothiocyanate analogue thereof to a human, wherein said isothiocyanate analog comprises an isothiocyanate moiety and a polar functional group linked to the isothiocyanate moiety by a chain of one or more carbon atoms, and induces quinone reductase activity.

17. The method according to claim 16, wherein said sulforaphane or isothiocyanate analogue thereof is administered in oral, topical or parenteral dose form.

18. The method according to claim 16, wherein said sulforaphane or isothiocyanate analogue thereof is provided as a food, food supplement, or food additive.

19. The method according to claim 17, wherein said oral dose form is a pharmaceutical.

20. The method according to claim 16, wherein said sulforaphane or isothiocyanate analogue thereof is administered in topical or parenteral dose form.

21. A method for suppressing the formation of chemically-induced mammary tumors or hepatomas, comprising:

administering to a mammal a chemoprotective composition comprising sulforaphane ((−)1-isothiocyanato-(4R)-(methylsulfinyl)butane) or an analogue thereof, said analogue being selected from the group consisting of: 6-isothiocyanato-2-hexanone; exo-2-acetyl-6-isothiocyanatonorbornane; exo-2-isothiocyanato-6-methylsulfonylnorbornane; 6-isothiocyanato-2-hexanol; 1-isothiocyanato-4-dimethylphosphonylbutane; exo-2-(1'-hydroxyethyl)-5-isothiocyanatonorbornane; exo-2-acetyl-5-isothiocyanatonorbornane; 1-isothiocyanato-5-methylsulfonylpentane; and cis- or trans-3-(methylsulfonyl) cyclohexylmethylisothiocyanate, and a suitable excipient.

22. The composition of claim 15, wherein said active ingredient is sulforaphane ((−)-isothiocyanato-(4R)-(methylsulfinyl)butane).

23. The method of claim 17, wherein said oral dose form is a dietary supplement.

24. The composition of claim 1, wherein said composition is in oral, topical or parenteral dose form.

25. The composition of claim 15, wherein said composition is in oral, topical or parenteral dose form.

26. The composition of claim 1, wherein said composition is a dietary supplement.

27. The composition of claim 15, wherein said composition is a dietary supplement.

28. The composition of claim 1, wherein said composition is incorporated into a food product.

29. The composition of claim 15, wherein said composition is incorporated into a food product.

30. The composition of claim 1, wherein said composition is a food supplement or food additive.

31. The composition of claim 15, wherein said composition is a food supplement or food additive.

32. The composition of claim 24, wherein said dosage form is a pharmaceutical.

33. The composition of claim 25, wherein said dosage form is a pharmaceutical.

34. A method of chemoprotection comprising the steps of:

(a) extracting sulforaphane or an isothiocyanate analogue thereof from a natural source; and (b) providing said sulforaphane or isothiocyanate analogue thereof to a human, wherein said isothiocyanate analog comprises an isothiocyanate moiety and a polar functional group linked to the isothiocyanate moiety by a chain of one or more carbon atoms, and induces quinone reductase activity.

35. A method of chemoprotection comprising administering to said human a composition comprising an active ingredient which is sulforaphane ((−)-1-isothiocyanato-(4R)-(methylsulfinyl)butane) or an analogue thereof, said analogue being selected from the group consisting of: 6-isothiocyanato-2-hexanone; exo-2-acetyl-6-isothiocyanatonorbornane; exo-2-isothiocyanato-6-methylsulfonylnorbornane; 6-isothiocyanato-2-hexanol; 1-isothiocyanato-4-dimethylphosphonylbutane; exo-2-(1'-hydroxyethyl)-5-isothiocyanatonorbornane; exo-2-acetyl-5-isothiocyanatonorbornane; 1-isothiocyanato-5-methylsulfonylpentane; and cis- and trans-3-(methylsulfonyl)cyclohexylmethylisothiocyanate, and a suitable excipient.

36. A method of chemoprotection comprising administering to said human a composition comprising an active ingredient which is an analogue of sulforaphane ((−)-1-isothiocyanato-(4R)-(methylsulfinyl)butane) selected from the group consisting of 6-isothiocyanato-2-hexanone, exo-2-acetyl-6-isothiocyanatonorbornane, exo-2-isothiocyanato-6-methylsulfonylnorbornane, 6-isothiocyanato-2-hexanol; 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, and cis- or trans-3-(methylsulfonyl) cyclohexylmethylisothiocyanate.

37. A method of stimulating mammalian enzymes involved in detoxification of carcinogens, comprising administering to said mammal a chemoprotective composition comprising sulforaphane ((−)1-isothiocyanato-(4R)-(methylsulfinyl) butane) or an analogue thereof, said analogue being selected from the group consisting of: 6-isothiocyanato-2-hexanone; exo-2-acetyl-6-isothiocyanatonorbornane; exo-2-isothiocyanato-6-methylsulfonylnorbornane; 6-isothiocyanato-2-hexanol; 1-isothiocyanato-4-dimethylphosphonylbutane; exo-2-(1'-hydroxyethyl)-5-isothiocyanatonorbornane; exo-2-acetyl-5-isothiocyanatonorbornane; 1-isothiocyanato-5-methylsulfonylpentane; and cis- or trans-3-(methylsulfonyl) cyclohexylmethylisothiocyanate, and a suitable excipient.

38. A method of stimulating mammalian enzymes involved in detoxification of carcinogens, comprising administering to said mammal a composition comprising an active ingredient which is an analogue of sulforaphane ((−)1-isothiocyanato-(4R)-(methylsulfinyl)butane) selected from the group consisting of 6-isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, and cis- or trans-3-(methylsulfonyl) cyclohexylmethylisothiocyanate.

39. A method of protecting a mammal against the toxic and neoplastic effects of carcinogens, comprising administering to said mammal a chemoprotective composition comprising sulforaphane ((−)-isothiocyanato-(4R)-(methylsulfinyl)butane) or an analogue thereof, said analogue being selected from the group consisting of: 6-isothiocyanato-2-hexanone; exo-2-acetyl-6-isothiocyanatonorbornane; exo-2-isothiocyanato-6-methylsulfonylnorbornane; 6-isothiocyanato-2-hexanol; 1-isothiocyanato-4-dimethylphosphonylbutane; exo-2-(1'-hydroxyethyl)-5-isothiocyanatonorbornane; exo-2-acetyl-5-isothiocyanatonorbornane; 1-isothiocyanato-5-

*methylsulfonylpentane; and cis- or trans-3-(methylsulfonyl) cyclohexylmethylisothiocyanate, and a suitable excipient.*

*40. A method of protecting a mammal against the toxic and neoplastic effects of carcinogens, comprising administering to said mammal a composition comprising an active ingredients which is an analogue of sulforaphane ((−)1-isothiocyanato-(4R)-(methylsulfinyl)butane) selected from the group consisting of 6-isothiocyanato-2-hexanone, exo-2-acetyl-6-isothiocyanatonorbornane, exo-2-isothiocyanato-6-methylsulfonylnorbornane, 6-isothiocyanato-2-hexanol; 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, and cis- or trans-3-(methylsulfonyl) cyclohexylmethylisothiocyanate.*

*41. A method of inducing phase II xenobiotic metabolizing enzymes, comprising administering to said mammal a chemoprotective composition comprising sulforaphane ((−) 1-isothiocyanato-(4R)-(methylsulfinyl)butane) or an analogue thereof, said analogue being selected from the group consisting of: 6-isothiocyanato-2-hexanone; exo-2-acetyl-6-isothiocyanatonorbornane; exo-2-isothiocyanato-6-methylsulfonylnorbornane; 6-isothiocyanato-2-hexanol; 1-isothiocyanato-4-dimethylphosphonylbutane; exo-2-(1'-hydroxyethyl)-5-isothiocyanatonorbornane; exo-2-acetyl-5-isothiocyanatonorbornane; 1-isothiocyanato-5-methylsulfonylpentane; and cis- or trans-3-(methylsulfonyl) cyclohexylmethylisothiocyanate, and a suitable excipient.*

*42. A method of inducing phase II xenobiotic metabolizing enzymes, comprising administering to said mammal a composition comprising an active ingredient which is an analogue of sulforaphane ((−)1-isothiocyanato-(4R)-(methylsulfinyl)butane) selected from the group consisting of 6-isothiocyanato-2-hexanone, exo-2-acetyl-6-isothiocyanatonorbornane; exo-2-isothiocyanato-6-methylsulfonylnorbornane, 6-isothiocyanato-2-hexanol; 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, and cis- or trans-3-(methylsulfonyl) cyclohexylmethylisothiocyanate.*

*43. The method according to claim 16, wherein said isothiocyanate analog is selected from the group consisting of 6-isothiocyanato-2-hexanone, exo-2-acetyl-6-isothiocyanatonorbornane, exo-2-isothiocyanato-6-methylsulfonylnorbornane, 6-isothiocyanato-2-hexanol; 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, and cis- or trans-3-(methylsulfonyl) cyclohexylmethylisothiocyanate.*

*44. The method according to claim 34, wherein said isothiocyanate analog is selected from the group consisting of 6-isothiocyanato-2-hexanone, exo-2-acetyl-6-isothiocyanatonorbornane, exo-2-isothiocyanato-6-methylsulfonylnorbornane, 6-isothiocyanato-2-hexanol; 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, and cis- or trans-3-(methylsulfonyl) cyclohexylmethylisothiocyanate.*

*45. A composition comprising an isothiocyanate analogue of sulforaphane ((−)1-isothiocyanato(4R)-(methylsulfinyl) butane), wherein said isothiocyanate analog comprises an isothiocyanate moiety and a polar functional group linked to the isothiocyanate moiety by a chain of one or more carbon atoms, and induces quinone reductase activity.*

*46. A composition comprising an active ingredient which is sulforaphane ((−)1-isothiocyanato-(4R)-(methylsulfinyl) butane) or an isothiocyanate analogue thereof and a suitable excipient, wherein said isothiocyanate analog comprises an isothiocyanate moiety and a polar functional group linked to the isothiocyanate moiety by a chain of one or more carbon atoms, and induces quinone reductase activity.*

*47. The method of promoting human health comprising the steps of:*

*(a) extracting sulforaphane or an analogue thereof from a natural source; and*

*(b) providing said sulforaphane or analogue thereof to a human.*

* * * * *